United States Patent
Doguchi et al.

(10) Patent No.: US 7,393,321 B2
(45) Date of Patent: Jul. 1, 2008

(54) ENDOSCOPE APPARATUS WITH SOLID-STATE PICK-UP

(75) Inventors: Nobuyuki Doguchi, Hino (JP); Yoshinori Takahashi, Hachioji (JP); Katsuichi Imaizumi, Hachioji (JP); Takeshi Ozawa, Sagamihara (JP); Sakae Takehana, Sagamihara (JP); Isami Hirao, Hachioji (JP)

(73) Assignee: Olympus Corporation, Tokyo (JP)

( * ) Notice: Subject to any disclaimer, the term of this patent is extended or adjusted under 35 U.S.C. 154(b) by 783 days.

(21) Appl. No.: 10/871,223

(22) Filed: Jun. 18, 2004

(65) Prior Publication Data

US 2005/0010081 A1 Jan. 13, 2005

(30) Foreign Application Priority Data

Jun. 18, 2003 (JP) .............................. 2003-174001

(51) Int. Cl.
*A61B 1/045* (2006.01)
(52) U.S. Cl. ...................... 600/109; 600/118; 600/160; 348/70; 348/74
(58) Field of Classification Search ................ 600/109, 600/118, 160; 348/65, 70, 72, 74, 296, 297
See application file for complete search history.

(56) References Cited

U.S. PATENT DOCUMENTS

| | | | | |
|---|---|---|---|---|
| 4,007,488 A | * | 2/1977 | Morishita et al. | 348/223.1 |
| 5,001,556 A | * | 3/1991 | Nakamura et al. | 348/70 |
| 5,337,340 A | | 8/1994 | Hynecek | |
| 5,912,764 A | * | 6/1999 | Togino | 359/367 |
| 6,425,858 B1 | | 7/2002 | Minami | |
| 6,638,215 B2 | * | 10/2003 | Kobayashi | 600/160 |
| 6,873,360 B1 | * | 3/2005 | Kawashiri | 348/296 |
| 2002/0042556 A1 | * | 4/2002 | Sugimoto et al. | 600/178 |
| 2003/0001952 A1 | * | 1/2003 | Iida et al. | 348/69 |
| 2003/0050532 A1 | * | 3/2003 | Doguchi | 600/109 |
| 2004/0210107 A1 | * | 10/2004 | Tani et al. | 600/109 |

FOREIGN PATENT DOCUMENTS

| | | |
|---|---|---|
| DE | 102 26 582 A1 | 12/2002 |
| EP | 0 534 1998 A2 | 3/1993 |
| EP | 1 258 221 A2 | 11/2002 |
| EP | 1 294 186 A2 | 3/2003 |
| JP | 10-309282 | 11/1998 |
| JP | 11-032982 | 2/1999 |
| JP | 11-137515 | 5/1999 |
| JP | 2000-5127 | 1/2000 |
| JP | 2001-29313 | 2/2001 |

* cited by examiner

*Primary Examiner*—John P Leubecker
(74) *Attorney, Agent, or Firm*—Scully, Scott, Murphy & Presser, P.C.

(57) ABSTRACT

An endoscope apparatus includes an endoscope that has a solid-state image-pickup device in which charges are accumulated in order to pick up an object image. The endoscope apparatus further comprises a memory in which a plurality of pieces of information on the accumulation period during which charges are accumulated in the solid-state image-pickup device is stored, and a drive unit that controls the accumulation period, during which charges are accumulated in the solid-state image-pickup device, on the basis of the pieces of information on the accumulation period stored in the memory. The endoscope further includes an optical member whose surface is shaped rotationally asymmetric. Correction information stored in a memory and associated with the optical element is used to correct an output signal of the solid-state image-pickup device.

31 Claims, 18 Drawing Sheets

FIG.2
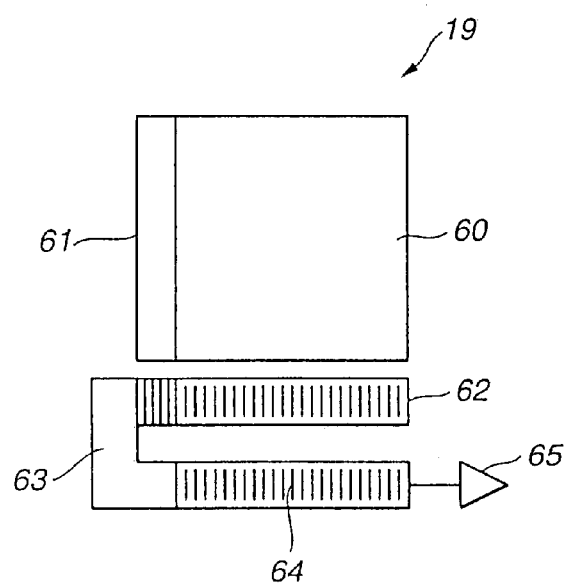
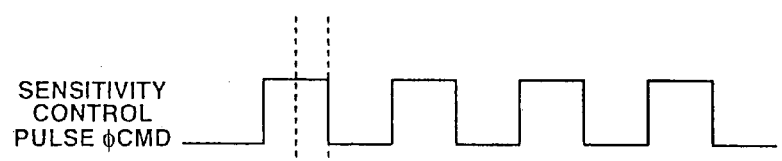
FIG.3A  SENSITIVITY CONTROL PULSE φCMD
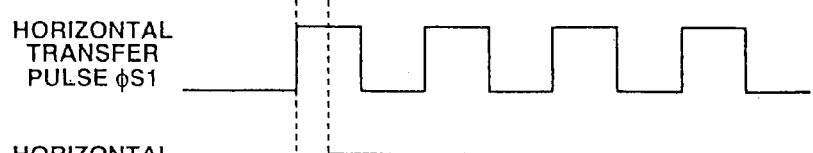
FIG.3B  HORIZONTAL TRANSFER PULSE φS1
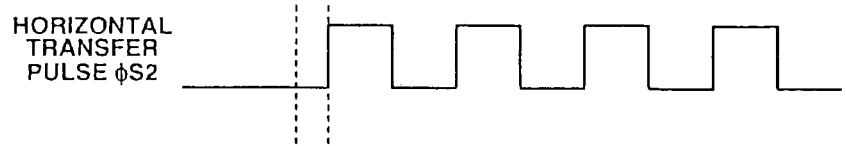
FIG.3C  HORIZONTAL TRANSFER PULSE φS2

ENDOSCOPE APPARATUS WITH SOLID-STATE PICK-UP

This application claims the benefit of Japanese Application No. 2003-174001 filed on Jun. 18, 2003, the contents of which are incorporated by reference.

BACKGROUND OF THE INVENTION

1. Field of the Invention

The present invention relates to an endoscope apparatus that acquires an image using an image pickup device in which charges are accumulated in order to pick up an object image.

2. Description of the Related Art

In general, endoscope apparatus for use in endoscopic examinations comprise an endoscope such as an electronic endoscope including a solid-state image-pickup device, a processor, a light source unit, and a monitor.

The conventional endoscope apparatus has an insertional unit of an endoscope inserted into a body cavity. Illumination light emanating from a light source unit is transmitted over a light guide, which is built in the endoscope, to illuminate an object. Light reflected from the object forms an optical image on a solid-state image-pickup device by an objective lens incorporated in the distal section of the endoscope. The solid-state image-pickup device photoelectrically converts the optical image. An output signal resulting from the photoelectric conversion is inputted in a processor serving as a signal processing apparatus. The processor performs signal processing. A video signal resulting from the signal processing is transmitted to a monitor to be displayed.

In recent years, a technique as follows has come to prevail: excitation light is irradiated to a region to be observed in a living-body tissue; and light caused by auto-fluorescence of the living-body tissue induced by the excitation light or light caused by fluorescence induced by an chemical agent injected into a living body is captured as a two-dimensional image by a solid-state image-pickup device. The fluorescence image is used to assess the condition of a lesion such as a carcinoma (kind of lesion or humectant range). Development of a fluorescence observation system for enabling observation of fluorescence is under way.

In auto-fluorescence, when excitation light is irradiated to a living-body tissue, the fluorescence is generated at the long wavelength side due to the excitation light. Fluorescence materials contained in a living body include, for example, nicotinamide adenine dinucleotide (NADH), flavine mononucleotide (FMN), and collagen. Recently, the correlation between diseases and materials that are intrinsic to living bodies and that generate fluorescence is being investigated. Observation of fluorescence enables diagnosis of carcinomas or the like.

Talking of chemifluorescence or fluorescence caused by a chemical agent, fluorescence substances to be injected into a living body include hematoporphyrin (HpD), photofrin, and α-amino levulinic acid (ALA). These chemical agents have a specific property of accumulating in a carcinoma or the like. Therefore, when any of the agents is injected preliminarily into a living body in order to observe fluorescence, a lesion can be diagnosed. Other technique is such that a fluorescence substance is administered to a monoclonal antibody and accumulated in a lesion by utilizing antigen-antibody reaction.

A fluorescence observation system disclosed in Japanese Unexamined Patent Application Publication No. 2001-29313 aims at acquisition of a fluorescence monochrome image, in the system, the sensitivity of a CCD incorporated in the distal section of an endoscope is varied and controlled such that the average brightness values exhibited by a fluorescence image, that is, the average brightness of an image displayed on a monitor will remain constant.

According to the conventional fluorescence observation system, when excitation light is irradiated to the mucosa of the bronchus or the alimentary tract, auto-fluorescence occurs. The intensity of light caused by auto-fluorescence is much feebler than that of reflected light resulting from irradiation of normal illumination light. Moreover, the ratio of the intensity of auto-fluorescence to the intensity of reflected light may greatly vary depending on a region such as the superior alimentary tract (esophagus and stomach) or the inferior alimentary track (large intestine).

SUMMARY OF THE INVENTION

An-endoscope apparatus in accordance with the present invention comprises: an endoscope having a solid-state image-pickup device in which charges are accumulated in order to pick up an object image; a memory in which a plurality of pieces of information on the accumulation period during which charges are accumulated in the solid-state image-pickup device are stored; and a drive unit that controls the accumulation period, during which charges are accumulated in the solid-state image-pickup device, on the basis of the pieces of information on the accumulation period stored in the memory.

BRIEF DESCRIPTION OF THE DRAWINGS

FIG. 1 to FIG. 11B are concerned with a first embodiment of the present invention; FIG. 1 is a block diagram schematically showing the configuration of an endoscope apparatus in accordance with a first embodiment of the present invention;

FIG. 2 is a block diagram showing a solid-state image-pickup device realized with a charge-coupled device and employed in the first embodiment of the present invention;

FIG. 3A, FIG. 3B, and FIG. 3C are timing charts indicating the timings of a sensitivity control pulse $\phi$CMD and horizontal transfer pulses $\phi$S1 and $\phi$S2;

FIG. 4 is an explanatory diagram showing the relationship between a CMD applied voltage and a CMD amplification factor that relate to the sensitivity of a CCD;

FIG. 5A to FIG. 5F indicate timings to signify the actions to be performed in order to drive a CCD in a special light mode;

FIG. 6A to FIG. 6F indicate timings to signify the actions to be performed in order to drive a CCD in a normal light mode;

FIG. 7 is a graph indicating the property or sensitivity of a CCD (output signal to be sent to a monitor);

FIG. 8 is a graph indicating the property or sensitivity of a CCD (signal-to-noise ratio);

FIG. 9 is a plan view showing the structure of an RGB rotary filter;

FIG. 10 is a graph indicating the spectral characteristic of light emitted from a light source unit during fluorescence observation;

FIG. 11B is a flowchart describing the outline of a process to be executed in the first embodiment;

FIG. 14 is a block diagram schematically showing an endoscope apparatus in accordance with the fourth embodiment of the present invention;

FIG. 15A to FIG. 15E indicate timings to signify the actions to be performed in order to drive a CCD;

FIG. 16 is a plan view showing the structure of an RGB rotary filter;

FIG. 17 is a graph indicating the spectral characteristic of light emitted from a light source unit during narrow-band light observation;

FIG. 18 is a graph indicating the spectral characteristic of reflected light employed in narrow-band light observation;

DESCRIPTION OF THE PREFERRED EMBODIMENTS

Figure 1:
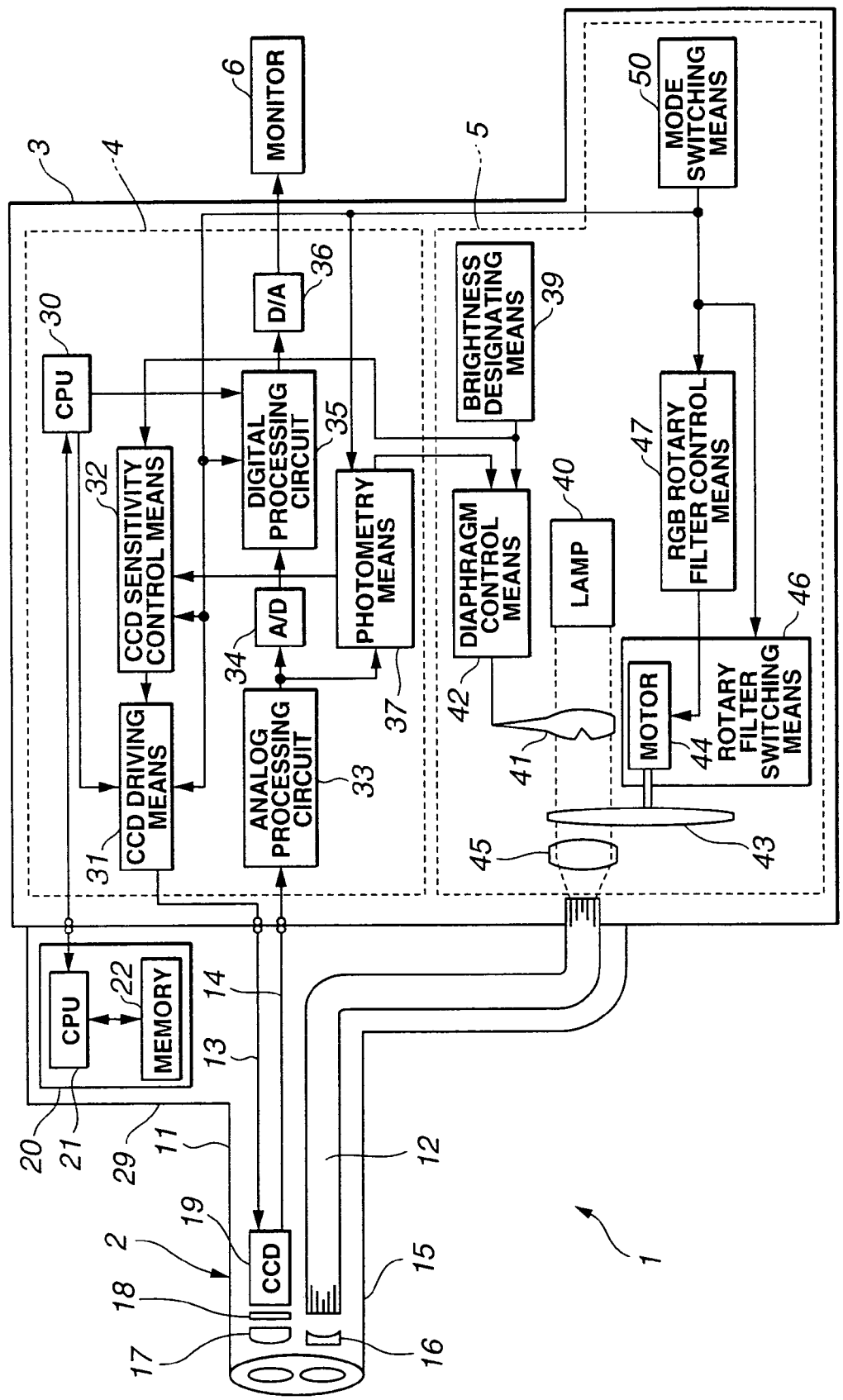

Referring to the drawings, embodiments of the present invention will be described below.

First Embodiment

Referring to FIG. 1 to FIG. 11, a first embodiment of the present invention will be described below.

(Configuration)

To begin with, the configuration of the first embodiment will be described below.

As shown in FIG. 1, an endoscope apparatus 1 in accordance with the first embodiment comprises an electronic endoscope (hereinafter, an endoscope) 2, a processor 3, and a monitor 6.

The endoscope 2 is freely detachably connected to the processor 3. Moreover, the processor 3 includes a signal processing unit 4 and a light source unit 5. The light source unit may be separated from the processor.

The monitor 6 is connected to the processor 3. A video signal treated by the processor 3 is transmitted to the monitor 6.

The endoscope 2 has an elongated insertional unit 11 that is inserted into a patient's body cavity.

For examination of the alimentary tract, bronchus, craniocervix (pharynx), or bladder, the insertional unit 11 is formed with a soft member. For examination of the abdominal or thoracic cavity or the uterus, the insertional unit 11 is formed with a rigid member.

Moreover, the endoscope 2 has a charge-coupled device (hereinafter CCD) 19, which includes a facility for varying an amplification factor as described later, as a solid-state image-pickup device incorporated in the distal section 15 of the insertional unit 11.

A light guide 12 by which illumination light is transmitted, a CCD driving signal line 13 by which a CCD driving signal is transmitted and which is coupled to the CCD 19, and a CCD output signal line 14 by which a CCD output signal resulting from photoelectric conversion performed by the CCD 19 is transmitted are run through the insertional unit 11.

The distal end of the light guide 12 is fixed in the distal section 15 of the insertional unit 11. An illumination lens 16 is arranged on an illumination window opposite to the distal end of the light guide.

By the light guide 12, illumination light emanating from the light source unit 5 is transmitted to the distal end of the light guide 12. An object such as an intracavitary lesion is illuminated with the illumination light emitted from the distal end through the illumination lens 16.

An objective lens 17, an excitation light cut filter 18, and the CCD 19 are arranged behind an observation (image picking-up) window adjoining the illumination window in the distal section 15.

The objective lens 17 forms an optical image of an object on the image picking-up (light receiving) surface of the CCD 19 that serves as an image sensor and that is located at the position of the image plane.

The excitation light cut filter 18 is located in front of the CCD 19, and passes light, of which wavelengths fall within a specific band, that is, fluorescence alone. According to the present embodiment, the excitation light cut filter 18 has a property of passing auto-fluorescence (whose wavelengths are equal to or higher than 500 nm) caused by fluorescence of a living-body tissue but of intercepting excitation light.

In other words, according to the present embodiment, light reflected from an object and auto-fluorescence caused by fluorescence of the object form images on the light receiving surface of the CCD 19 via the objective lens 17 and excitation light cut filter 18.

Referring to FIG. 1, an illumination and image-pickup optical system, that is, an optical system including the illumination lens 16, objective lens 17, CCD 19, and the like is disposed in order to realize an endoscope of a direct-vision type that emits illumination light forward in the longitudinal direction of the insertional unit 11 and that offers a field of view for observation (image picking-up) in the forward direction. Alternatively, the optical system may be disposed in order to realize an endoscope of an oblique-vision or side-vision type.

Moreover, the CCD 19 is connected to CCD driving means 31 included in the signal processing unit 4 incorporated in the processor 3 via the driving signal line 13. When a driving signal produced by the CCD driving means 31 is applied to the CCD 19, an electronic shutter is controlled, signal charges are accumulated, the sensitivity of the CCD 19 is controlled, and image data is read.

An object image formed on the light receiving surface of the CCD 19 by the objective lens 17 and excitation light cut filter 18 is photoelectrically converted pixel by pixel by the CCD 19. Thereafter, the resultant signal is transferred and transmitted from a floating diffusion amplifier. The output signal of the CCD 19 is transferred to an analog processing circuit 33 included in the signal processing unit 4 incorporated in the processor 3 via the CCD output signal line 14.

Moreover, a storage device 20 is incorporated inside, for example, a connector 29 formed at the proximal end of the endoscope 2. The storage device 20 may be incorporated inside, for example, an operating unit or the like other than the connector 29. The storage device 20 comprises a CPU 21 and a memory 22.

The memory 22 is formed with, for example, a nonvolatile EEPROM, a flash memory, or any other electrically reprogrammable semiconductor memory. Data can be electrically written in or read from the memory 22.

The CPU 21 controls reading or writing of data in or from the memory 22, and controls transmission or reception (communication) of data to or from the processor 3.

The accumulation periods (electronic shutter speeds) during which charges are accumulated responsively to three kinds of wavelength of red, green, and blue in a normal light mode, and the accumulation periods (electronic shutter speeds) during which charges are accumulated responsively to three kinds of wavelength Ex1 (fluorescence), Ex2 (green reflected light), and Ex3 (red reflected light) in a special light mode (fluorescence observation) are stored in the memory 22.

Instead of the accumulation periods, a charge clear period, a ratio of the accumulation periods during which charges are accumulated responsively to three kinds of wavelength of red, green, and blue or three kinds of wavelength Ex1, Ex2, and Ex3 may be stored in the memory 22.

As for the accumulation periods during which charges are accumulated responsively to a fluorescence wavelength and two kinds of reflected light wavelength and which are stored in the memory 22, the accumulation period during which charges are accumulated responsively to fluorescence is set longer than those during which charges are accumulated responsively to two kinds of respective reflected light wavelength.

The accumulation periods during which charges are accumulated responsively to three kinds of wavelength of red, green, and blue in the normal light mode and which are stored in the memory 22 are set shorter than those determined for an endoscope including a typical CCD other than a sensitivity-valiable CCD serving as the CCD 19.

The accumulation periods during which charges are accumulated responsively to three kinds of wavelength in the special light mode and which are stored in the memory 22 are set to optimal values according to whichever of types of endoscopes (for examination of the bronchus, superior alimentary tract, inferior alimentary tract, cranio-cervix, or bladder) is adopted. This is because the intensities of fluorescence and reflected light differ from region to region. The accumulation periods are determined for the three kinds of wavelength in relation to each region such that the intensities will remain at equal levels.

Aside from the accumulation periods, other data relevant to the endoscope is stored in the memory 22.

The stored data includes, for example, an endoscope model (type) name, an endoscope serial number, white balance set values (for normal lights and for special lights (fluorescence observation)), the number of times by which the endoscope is connected to the processor and the power supply thereof is turned on, information on a forceps channel lying through the endoscope, the outer diameter of the distal section of the endoscope, and the outer diameter of the insertional unit of the endoscope.

According to the present embodiment, the signal processing unit 4 comprises a CPU 30, CCD driving means 31, a CCD sensitivity control means 32, an analog processing circuit 33, an analog-to-digital (A/D) converter 34, a digital processing circuit 35, a digital-to-analog (D/A) converter 36, and a photometry means 37.

The light source unit 5 comprises a lamp 40, a diaphragm 41, diaphragm control means 42, an RGB rotary filter 43, a motor 44, a condenser lens 45, a rotary filter switching means 46, an RGB rotary filter control means 47, and a mode switching means 50.

When a user connects the endoscope 2 to the processor 3, the CPU 30 controls to read various kinds of data from the memory 22 via the CPU 21. In this case, the various kinds of data stored in the memory 22 are transmitted to the CPU 30 via the CPU 21. The CPU 30 reads various kinds of data from the memory 22.

Moreover, the CPU 30 transmits to the CCD driving means 31 the data representing accumulation periods, during which charges are accumulated responsively to three kinds of wavelength in the normal light mode and special light mode alike (fluorescence observation), and which are obtained from the memory 22.

Furthermore, the CPU 30 transmits the endoscope model name, serial number, white balance set values (for normal light and for special light), and others to the digital processing circuit 35.

Next, the CCD 19 will be described below.

The CCD 19 employed in the present embodiment is realized with a sensitivity-variable CCD that utilizes an impact ionization phenomenon and that is described in, for example, the U.S. Pat. No. 5,337,340 "Charge Multiplying Detector (CMD) suitable for small pixel CCD image sensors."

The CCD 19 has a charge multiplying detector interposed between a horizontal transfer register and a floating diffusion amplifier therein or disposed at each of pixel locations therein. When the processor 3 applies a pulse of a high-strength electric field to the charge multiplying detector, each signal charge gains energy from the high-strength electric field and collides with electrons in the valence band. Consequently, impact ionization occurs to produce a new signal charge (secondary electron).

For example, when an avalanche condition is utilized, application of one pulse causes a chain reaction to produce a secondary electron. When impact ionization is utilized, application of a relatively low-voltage pulse causes production of a hole-electron pair.

If the CCD 19 has the charge multiplying detector disposed in a stage preceding the floating diffusion amplifier, the number of signal charges can be freely increased by controlling the voltage level (amplitude) of a pulse to be applied.

On the other hand, when the charge multiplying detector is disposed at each of the pixel locations, the number of signal charges can be freely increased by controlling the voltage level (amplitude) of a pulse to be applied or the number of pulses to be applied.

In the present embodiment, a monochrome CCD of a full frame transfer (FFT) type having, as shown in FIG. 2, a charge multiplying detector interposed between a horizontal transfer register and a floating diffusion amplifier is adopted as the CCD 19.

The CCD 19 includes an image area 60, an optical black (OB) section 61, a horizontal transfer register 62, a dummy 63, a charge multiplying detector 64, and a floating diffusion amplifier 65. The charge multiplying detector 64 comprises nearly the same number of cells as the number of cells included in the horizontal transfer register 62 or comprises the number of cells that is twice larger than the number of cells included in the horizontal transfer register 62.

Signal charges produced at the respective pixel locations in the image area 60 are transferred to the horizontal transfer register 62 in response to vertical transfer pulses $\phi P1$ and $\phi P2$, which is shown in FIG. 5B, in units of signal charges juxtaposed on one horizontal line.

The signal charges transferred to the horizontal transfer register 62 are transferred to the dummy 63 and charge multiplying detector 64 in response to horizontal transfer pulses $\phi S1$ and $\phi S2$ that are shown in FIG. 3B and FIG. 3C (and FIG. 5D). A sensitivity control pulse $\phi CMD$ shown in FIG. 3A or FIG. 5C is applied to each of the plurality of cells constituting the charge multiplying detector 64, whereby the signal charges are transferred from one cell to an adjoining cell and are sequentially amplified step by step. The resultant signal charges are sequentially transferred to the floating diffusion amplifier 65.

The floating diffusion amplifier 65 converts the signal charges received from the charge multiplying detector 64 into a voltage signal, and transmits the signal as a CCD output signal to a component outside the CCD 19. Namely, the CCD output signal sent from the floating diffusion amplifier 65 is transferred to the processor 3 via the CCD output signal line 14.

According to the present embodiment, the phase correlation between the sensitivity control pulse φCMD and the horizontal transfer pulses φS1 and φS2 are, as shown in FIG. 3A to FIG. 3C, such that: before the horizontal transfer pulse φS1 rises, the sensitivity control pulse φCMD rises; and before the horizontal transfer pulse φS1 falls, the sensitivity control pulse φCMD falls. Moreover, when the sensitivity control pulse φCMD falls, the horizontal transfer pulse φS2 rises. When the sensitivity control pulse φCMD rises, the horizontal transfer pulse φS2 falls.

Sensitivity or an amplification factor obtained by the charge multiplying detector 64 can be varied by changing the voltage level (amplitude) of the sensitivity control pulse φCMD applied from the CCD driving means 31 to the charge multiplying detector 64.

Figure 4:
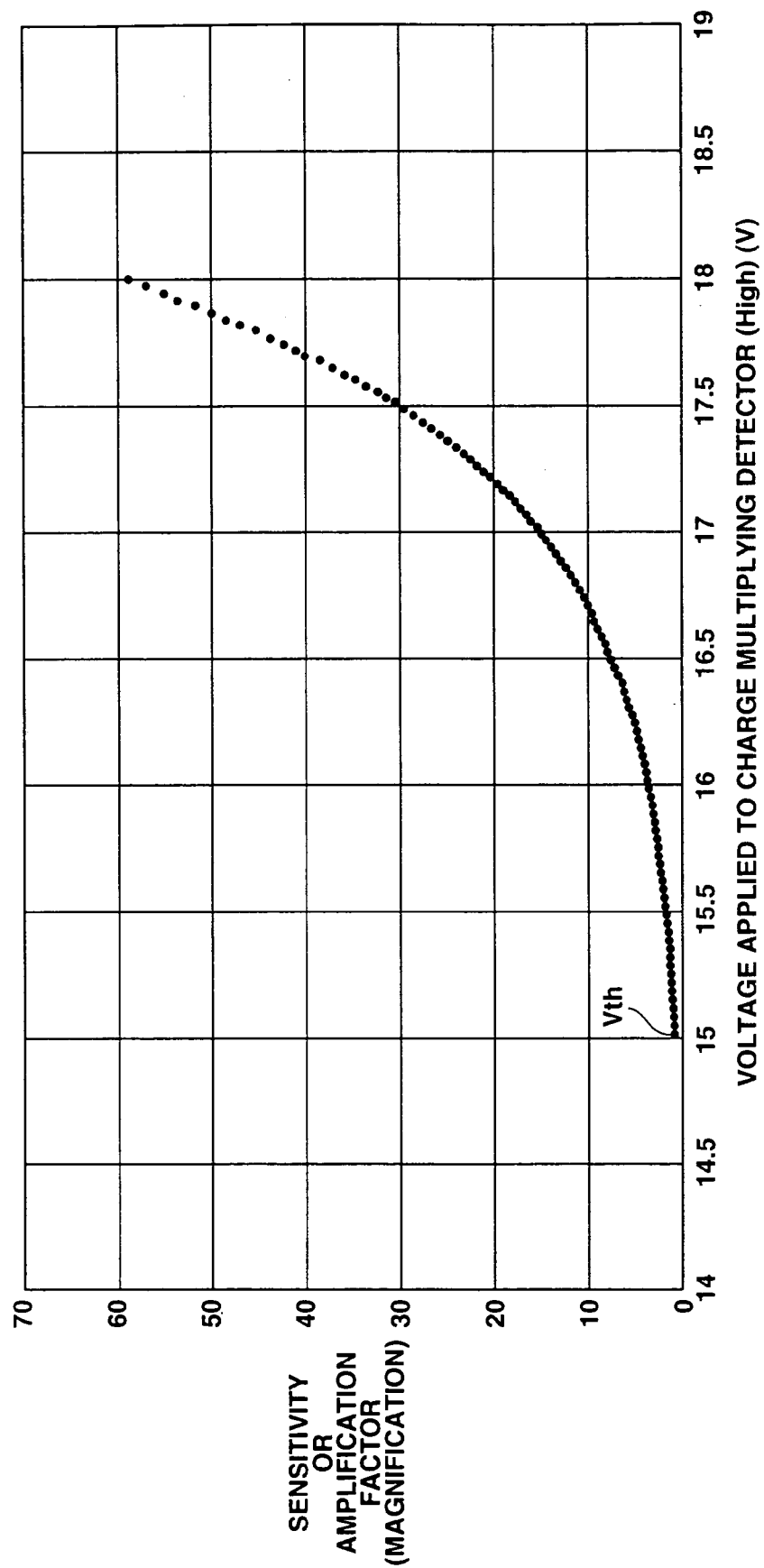
Figure 5:
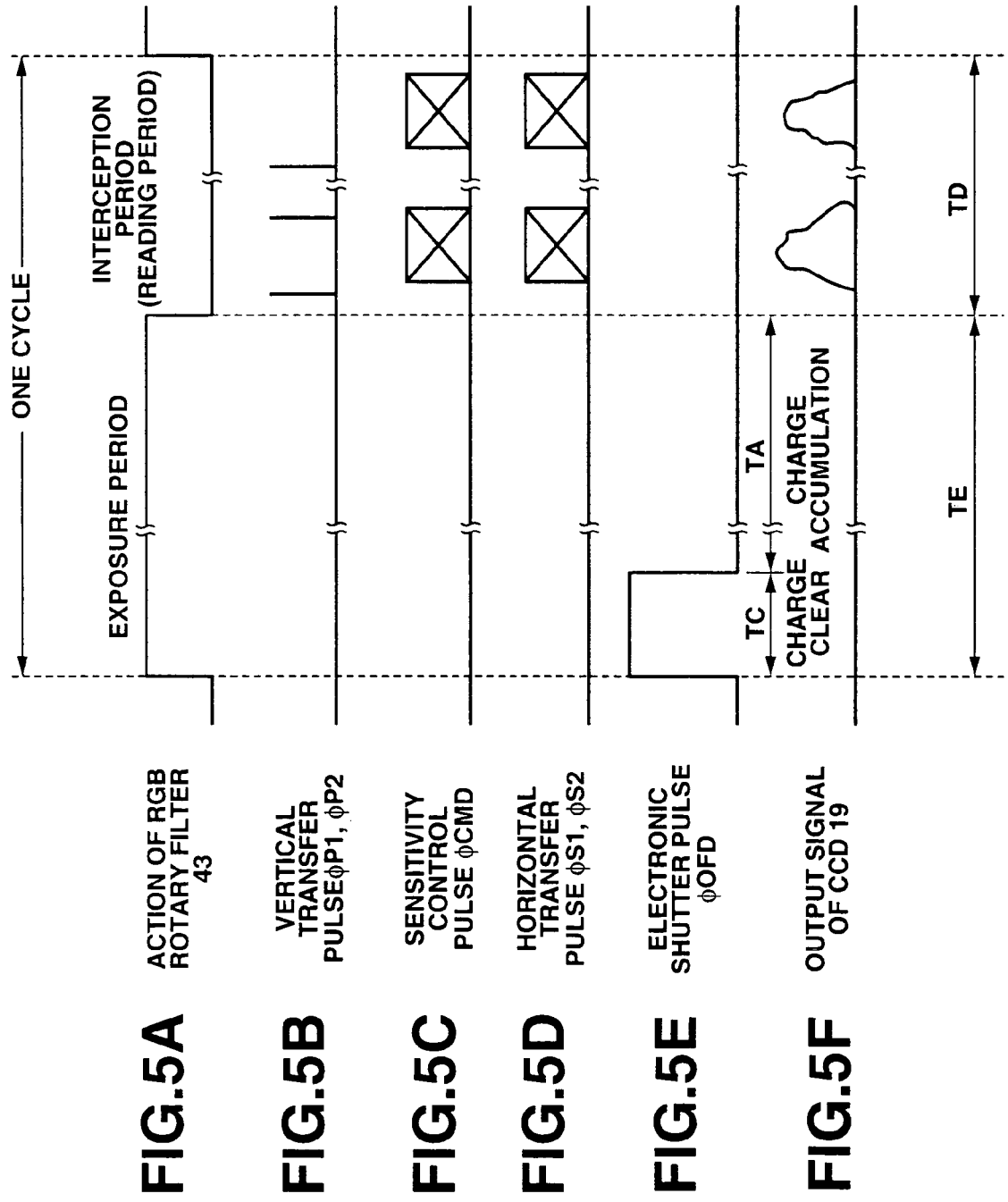

When the voltage to be applied to the charge multiplying detector 64 exceeds a certain threshold Vth, charge amplification starts and the sensitivity or amplification factor offered by the charge multiplying detector 64 exponentially increases as indicated in FIG. 4.

When the sensitivity control pulse φCMD ranges from (0)V to the threshold Vth, signal charges are not amplified but are merely transferred from the charge multiplying detector 64. The threshold that causes charge amplification to start or the sharpness in an increase in the sensitivity or amplification factor relative to the applied voltage can be varied in the stage of designing.

The CCD 19 has an electronic shutter facility. The principles of an electronic shutter lie in, like those of an electronic shutter included in a typical CCD, a substrate discharge technique that utilizes a change in an overflow characteristic caused by a variation of the voltage level (amplitude) of a pulse to be applied to an overflow drain.

During a period during which an electronic shutter pulse φOFD to be applied to the overflow drain is transferred to the CCD 19 (H-level), the signal charge at each of the pixel locations in the CCD 19 (including a noise charge) is released into a substrate. No signal charge is accumulated in each of the pixel locations in the CCD 19.

On the other hand, during a period during which the electronic shutter pulse φOFD is not transferred to the CCD 19, a signal charge is accumulated in each of the pixel locations in the CCD 19.

Moreover, since the pulse duration of the pulse φOFD and the number of pulses φOFD can be set to any values, the accumulation period during which signal charges are accumulated in the CCD 19 can be controlled to any period.

FIG. 5A to FIG. 5F indicate the timings of driving signals that are applied to the CCD 19 responsively to one of three kinds of wavelength in the special light mode, and the timing of an output signal of the CCD 19.

FIG. 5A indicates the action of the RGB rotary filter 43 in the special light mode. FIG. 5B indicates the timing of vertical transfer pulses φP1 and φP2 in the special light mode. FIG. 5C indicates the timing of a sensitivity control pulse φCMD in the special light mode. FIG. 5D indicates the timing of horizontal transfer pulses φS1 and φS2 in the special light mode.

FIG. 5E indicates the timing of an electronic shutter pulse φOFD in the special light mode. FIG. 5F indicates the timing of an output signal of the CCD 19 in the special light mode.

FIG. 6A to FIG. 6F indicate the timings of driving signals that are applied to the CCD 19 responsively to one of three kinds of wavelength in the normal light mode, and the timing of an output signal of the CCD 19. FIG. 6A indicates the action of the rotary filter 43 in the normal light mode. FIG. 6B indicates the timing of the vertical transfer pulses φP1 and φP2 in the normal light mode. FIG. 6C indicates the timing of the sensitivity control pulse φCMD in the normal light mode. FIG. 6D indicates the timing of the horizontal transfer pulses φS1 and φS2 in the normal light mode. FIG. 6E indicates the timing of an electronic shutter pulse φOFD in the normal light mode. FIG. 6F indicates the timing of an output signal of the CCD 19 in the normal light mode.

The CCD driving means 31 transmits as driving signals the vertical transfer pulses φP1 and φP2, sensitivity control pulse φCMD, horizontal transfer pulses φS1 and φS2, and electronic shutter pulse φOFD.

In FIG. 5A to FIG. 5F and FIG. 6A to FIG. 6F, one cycle refers to one cycle of one of three kinds of wavelength. Namely it refers to a one-third of one rotation of the action of the RGB rotary filter 43.

A period TE (special light mode) and a period TE' (normal light mode) refer to exposure periods. During the exposure period, the CCD 19 photoelectrically converts light that is reflected from an object and falls on the light receiving surface of the CCD 19, and then accumulates resultant signal charges.

During the period TD (special light mode) or TD' (normal light mode), the signal charges accumulated in the image area 60 during the period TE or TE' are transferred to the horizontal transfer register 62 in units of the signal charges juxtaposed on one horizontal line in response to the vertical transfer pulses φP1 and φP2. The signal charges are then transferred to the dummy 63, charge multiplying detector 64, and floating diffusion amplifier 65 in response to the horizontal transfer pulses φS1 and φS2. The floating diffusion amplifier 65 converts the charges into voltage levels, and a signal assuming the voltage levels is then transmitted.

In the special light mode, for the RGB rotary filter 43, the exposure period TE and interception period TD are, as shown in FIG. 5A, determined to constitute a one-cycle period.

The electronic shutter pulse φOFD shown in FIG. 5E has a pulse duration TC, during which it remains in H-level, at the beginning of the exposure period TE shown in FIG. 5A, whereby the charges at the respective pixel locations in the CCD 19 are cleared. Thereafter, the electronic shutter pulse φOFD goes low to thus indicate the start of a charge accumulation period TA during which charges are accumulated at the respective pixel locations in the CCD 19.

During the interception period TD that is a CCD 19 reading period shown in FIG. 5A, the CCD driving means 31 transmits the vertical transfer pulses φP1 and φP2 shown in FIG. 5B, the sensitivity control pulse φCMD shown in FIG. 5C, and the horizontal transfer pulses φS1 and φS2 shown in FIG. 5D. Consequently, the CCD 19 is read and an output signal of the CCD 19 shown in FIG. 5F is obtained.

The CCD driving means 31 varies the voltage level (amplitude) of the sensitivity control pulse φCMD shown in FIG. 5C according to data sent from the CCD sensitivity control means 32. The CCD driving means 31 transmits the sensitivity control pulse φCMD shown in FIG. 5C to the CCD 19, the sensitivity control pulse φCMD being in a certain phase relation with the horizontal transfer pulses φS1 and φS2 as shown in FIG. 5D (see FIG. 3A to FIG. 3C for details).

Consequently, in the special light mode, the CCD driving means 31 changes the voltage level (amplitude) of the sensitivity control pulse φCMD to be applied to the charge multiplying detector 64 and controls the CCD 19 such that a desired sensitivity or amplification factor can be attained.

In the normal light mode, for the RGB rotary filter 43, the exposure period TE' and interception period TD' are determined as shown in FIG. 6A within a one-cycle period.

The electronic shutter pulse φOFD shown in FIG. 6E has a pulse duration TC', during which it remains in H-level, at the beginning of the exposure period TE' shown in FIG. 6A, whereby the charges at the pixel locations in the CCD 19 will be cleared. Thereafter, the electronic shutter pulse φOFD goes low to thus indicate the start of the charge accumulation period TA' during which charges are accumulated at the respective pixel locations in the CCD 19.

During the interception period TD' shown in FIG. 6A that is the CCD 19 reading period TD', the CCD driving means 31 transmits the vertical transfer pulses φP1 and φP2 shown in FIG. 6B and the horizontal transfer pulses φS1 and φS2 shown in FIG. 6D. Consequently, the CCD 19 is read and an output signal of the CCD 19 shown in FIG. 6F is obtained.

In the normal light mode, the CCD driving means 31 does not transmit the sensitivity control pulse φCMD as shown in FIG. 6C. Otherwise, the CCD driving means 31 may transmit a sensitivity control pulse φCMD whose voltage level is equal to or lower than the threshold Vth.

Consequently, in the normal light mode, the charge multiplying detector 64 does not amplify charges and the sensitivity or amplification factor is set to 1 or a magnification of 1.

Figure 6:
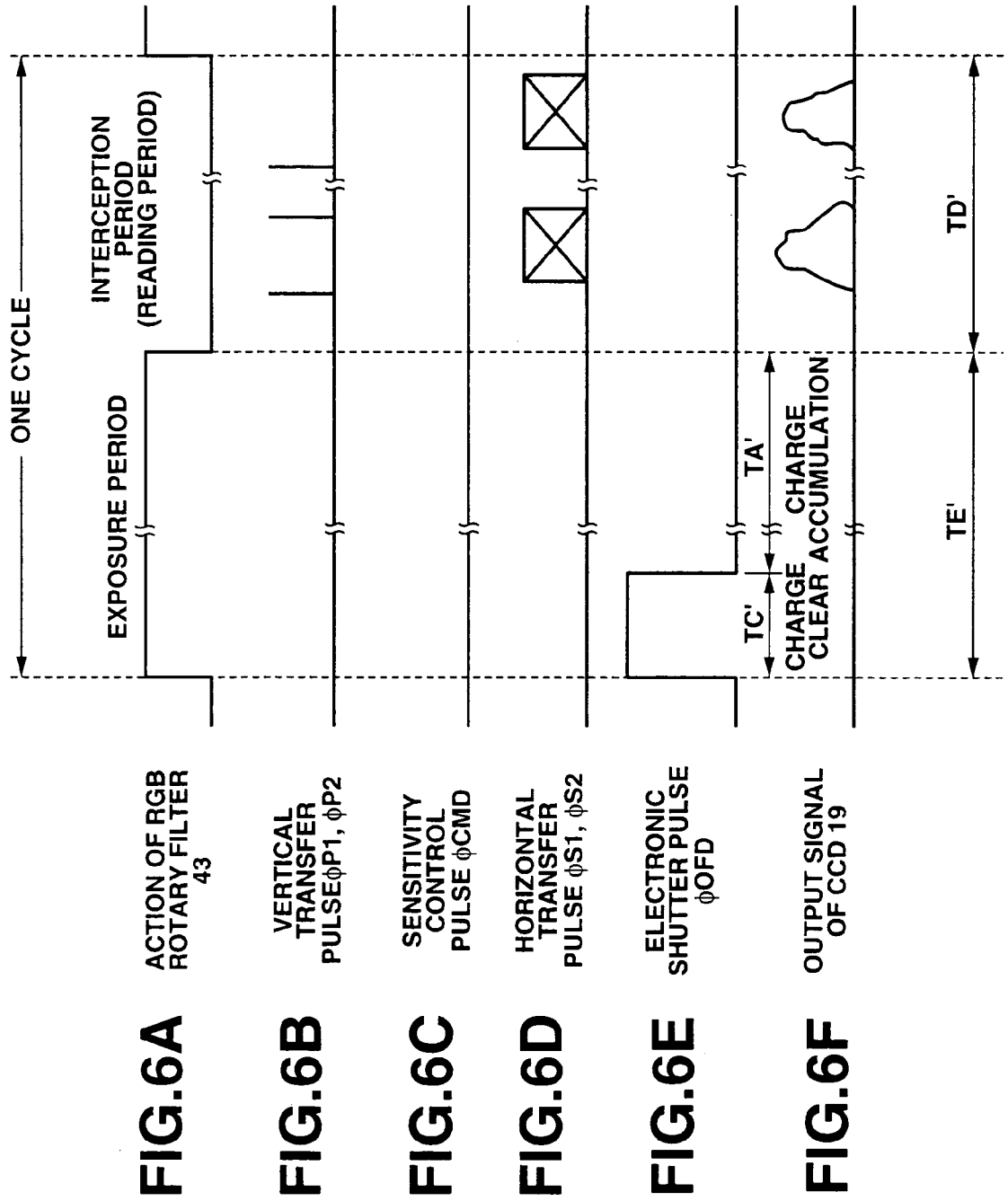

Incidentally, when a typical endoscope in which a sensitivity-valiable CCD such as the CCD 19 is not included is connected to the processor 3, the CCD driving means 31 performs actions defined for the normal light mode shown in FIG. 6.

The electronic shutter pulse φOFD shown in FIG. 5E and FIG. 6E is used to release the charges accumulated at the pixel locations into a substrate. The electronic shutter pulse φOFD having any pulse duration or any number of electronic shutter pulses φOFD is transmitted from the start of the exposure period (start of the interception period) to the end thereof.

The periods TE and TE' shown in FIG. 5A to FIG. 5F and FIG. 6A to FIG. 6F are periods during which charges are accumulated in the image area 60 of the CCD 19 according to an object image. During the periods TC and TC' corresponding to the pulse duration shown in FIG. 5E and FIG. 6E, no signal charge is accumulated.

When no electronic shutter pulse φOFD shown in FIG. 5E and FIG. 6E transmits, accumulation of signal charges at the respective pixel locations in the CCD 19 is started. The period TA (=period TE−period TC) (special light mode) or TA' (=period TE'−period TC') (normal light mode) from the start of the accumulation to the start of the interception period refers substantially to the accumulation period.

The electronic shutter pulse φOFD to be applied responsively to each light wavelength is transmitted to the CCD 19. Herein, the pulse duration and the number of electronic shutter pulses φOFD are determined based on the accumulation period, during which charges are accumulated responsively to each light wavelength from the CPU 30.

For example, assume that the three kinds of wavelength employed in the special light mode are three kinds of wavelength Ex1, Ex2, and Ex3, and that the accumulation periods during which charges are accumulated responsively to the three kinds of wavelength in the special light mode and which are stored in the memory 22 are TA(Ex1)=TE, TA(Ex2)=0.2*TE, and TA(Ex3)=0.1*TE respectively. In this case, these data representing the accumulation periods are transmitted to the CCD driving means 31 via the CPU 30. The pulse duration that is transmitted from the CCD driving means 31 to the CCD 19 in order to clear charges is set to OFD(Ex1)=0*TE, OFD(Ex2)=0.8*TE, or OFD(Ex3)=0.9*TE.

Moreover, assume that the accumulation periods during which charges are accumulated responsively to three kinds of wavelength in the normal line mode and which are stored in the memory 22 are, for example, TA'(R)=0.7*TE', TA'(G)=0.7*TE', and TA'(B)=0.7*TE' respectively. In this case, these data representing the accumulation periods are transmitted to the CCD driving means 31 via the CPU 30. The pulse duration that is transmitted from the CCD driving means 31 to the CCD 19 in order to clear charges is set to OFD(R)=OFD(G)=OFD(B)=0.3*TE'.

The analog processing circuit 33 includes a preamplifier that amplifies a CCD output signal of the CCD 19 and a Correlated Double Sampling (CDS) circuit that performs correlated double sampling so as to minimize a CCD noise. A signal resulting from CDS performed in the analog processing circuit 33 is transmitted to an A/D converter 34, and then converted into a digital form. An output of the A/D converter 34 is transmitted to the digital processing circuit 35.

The digital processing circuit 35 performs signal processing, such as clamping, white balance adjustment, color conversion, electronic zooming, gamma conversion, and image enhancement, on a video signal received from the A/D converter 34, and transmits the resultant signal to a D/A converter 36.

The D/A converter 36 converts the video signal received from the digital processing circuit 35 from the digital form into an analog form, and transmits the resultant signal.

Based on the analog video signal transmitted from the D/A converter 36, various kinds of images are displayed on the monitor 6. Moreover, the video signal transmitted from the D/A converter 36 is also transferred to an image recorder that is peripheral equipment and that is hot shown.

White balance adjustment and color conversion are different between the normal light mode and special light mode (fluorescence observation). The digital processing circuit 35 performs white balance adjustment and color conversion that are differentiated based on a mode switching signal sent from the mode switching means 50.

During color conversion in the special light mode (fluorescence observation), image data items produced based on a fluorescence wavelength and two kinds of reflected light wavelength are respectively multiplied by certain matrix coefficients. Consequently, a synthetic image is constructed based on the fluorescence wavelength and two kinds of reflected light wavelength.

Moreover, during white balance adjustment, white balance set values stored in the memory 22 are inputted to the digital processing circuit 35 via the CPU 30. Consequently, a white balance is attained in a different manner between the normal light mode and special light mode (fluorescence observation).

The photometry means 37 receives a video signal from the analog processing circuit 33, and calculates respective averages of brightness values exhibited by a screen image produced based on three kinds of wavelength of the normal light mode and special light mode (fluorescence observation).

Herein, the photometry means 37 calculates the average of brightness values by changing methods, which are associated with the normal light mode and special light mode (fluorescence observation), according to a mode switching signal sent from the mode switching means 50.

In the normal light mode, the photometry means 37 calculates a luminance signal level on the basis of the averages of the brightness values exhibited by screen images produced based on the three kinds of wavelength of red, green, and blue. The photometry means 37 then transmits the luminance signal to the diaphragm control means 42 included in the light source unit 5.

In the special light mode (fluorescence observation), the photometry means 37 calculates average values of brightness values exhibited by screen images produced based on three kinds of wavelength Ex1, Ex2, and Ex3, and generates an average of brightness values exhibited by a synthetic image constructed from the screen images produced based on the fluorescence wavelength and two kinds of reflected light wavelength. The generated average value is transmitted to the CCD sensitivity control means 32 and diaphragm control means 42 respectively.

The CCD sensitivity control means 32 controls the charge multiplying detector 64 included in the CCD 19 to execute automatic gain control (AGC) in the special light mode. The CCD sensitivity control means 32 controls the sensitivity or amplification factor offered by the charge multiplying detector 64 included in the CCD 19 such that an average of the levels of an output signal of the CCD 19 will be set to a desired value according to a change in the intensity of light reflected from an object and incident on the light receiving surface of the CCD 19.

The CCD sensitivity control means 32 receives from the photometry means 37 the average of brightness values, which are exhibited by a synthetic image constructed of a fluorescence image and reflected light images, and compares the average with an operator-designated monitor brightness level of an image to be displayed on the monitor.

An operator can designate a target value of a brightness level of a screen image to be displayed on the monitor using a brightness designating means 39 included in the light source unit 5. Incidentally, the brightness designating means 39 may be included in the signal processing unit 4.

The CCD sensitivity control means 32 compares the average of brightness values exhibited by a screen image with the operator-designated value (target value) of a brightness level. Based on the result of the comparison (whether the average of brightness values is larger or small), the CCD sensitivity control means 32 calculates the voltage level (amplitude) of the sensitivity control pulse φCMD, which the CCD driving means 31 transmits to the charge multiplying detector 64 included in the CCD 19, and transmits the voltage level to the CCD driving means 31.

An AGC method adopted by the CCD sensitivity control means 32 will be described below.

The relationship between the voltage level of the sensitivity control pulse φCMD to be transmitted to the charge multiplying detector 64 and the sensitivity or amplification factor, which is shown in FIG. 4, is approximated by the following expression:

$$M(V)=C \cdot \mathrm{Exp}\{\alpha(V-Vth)\} \tag{1}$$

Wherein, M(V) denotes the sensitivity or amplification factor attained when the voltage level (amplitude) of the sensitivity control pulse φCMD is V(v), and Vth denotes a threshold voltage that initiates charge amplification. C, α, and Vth denote constants inherent to each device and variable in the stage of designing.

When an image formed by light reflected from an object exhibiting a certain light intensity is picked up by a CCD, an average of brightness values exhibited by a screen image varies exponentially along with an increase or decrease in the voltage level of the sensitivity control pulse φCMD. Based on this fact, the CCD sensitivity control means 32 varies (increases or decreases) the voltage level (amplitude) of the sensitivity control pulse φCMD along with the changes in the intensities of light resulting from fluorescence of the object and of light reflected from the object such that the average of brightness values exhibited by a fluorescence image and an operator-designated target value of a brightness level of an image to be displayed on the monitor will be agreed with each other. Moreover, the CCD sensitivity control means 32 controls the CCD driving means 31 such that when the voltage level of the sensitivity control pulse φCMD is equal to or smaller than a threshold, an applied voltage will be 0(V).

Figure 7:
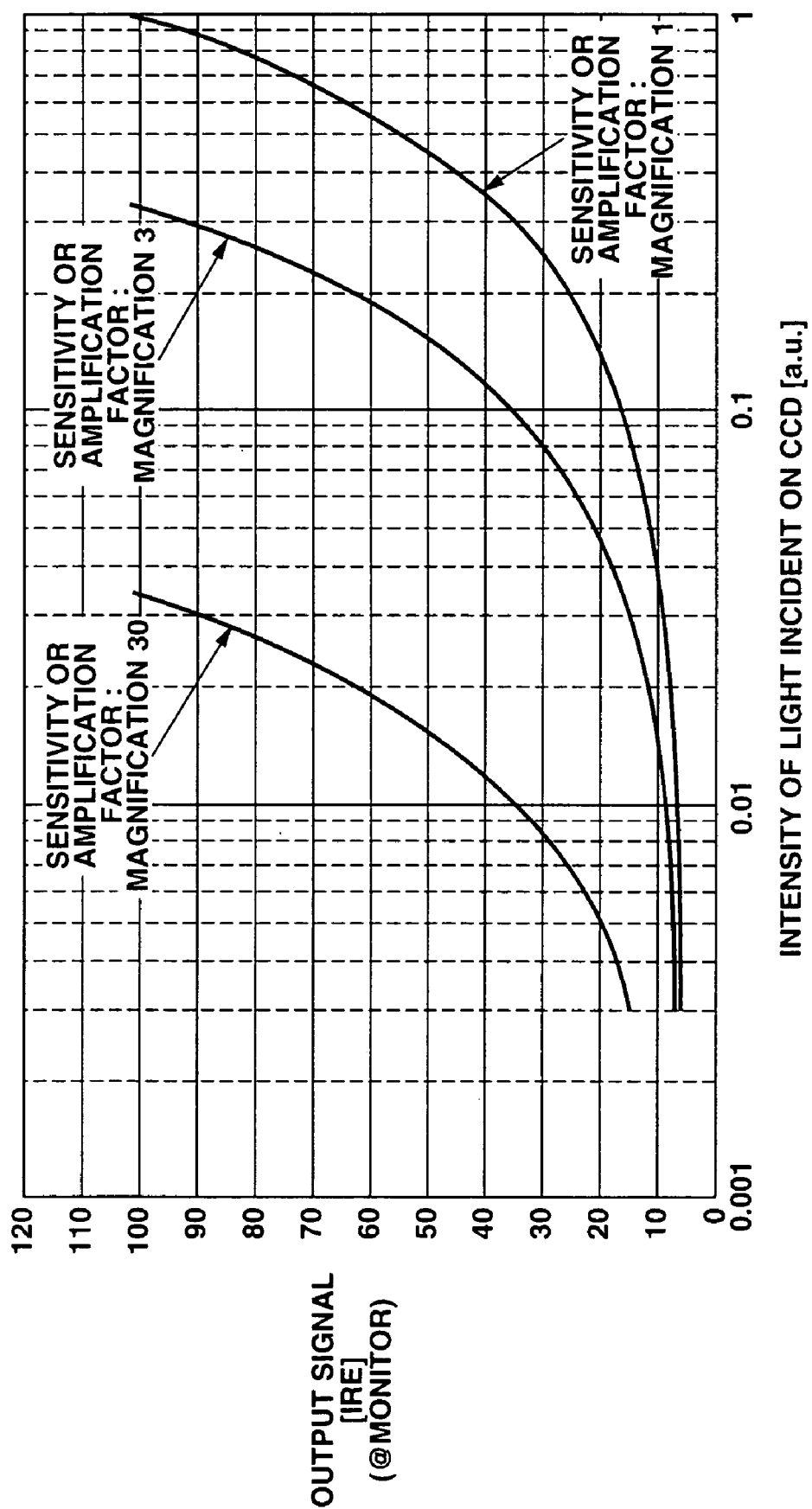
Figure 8:
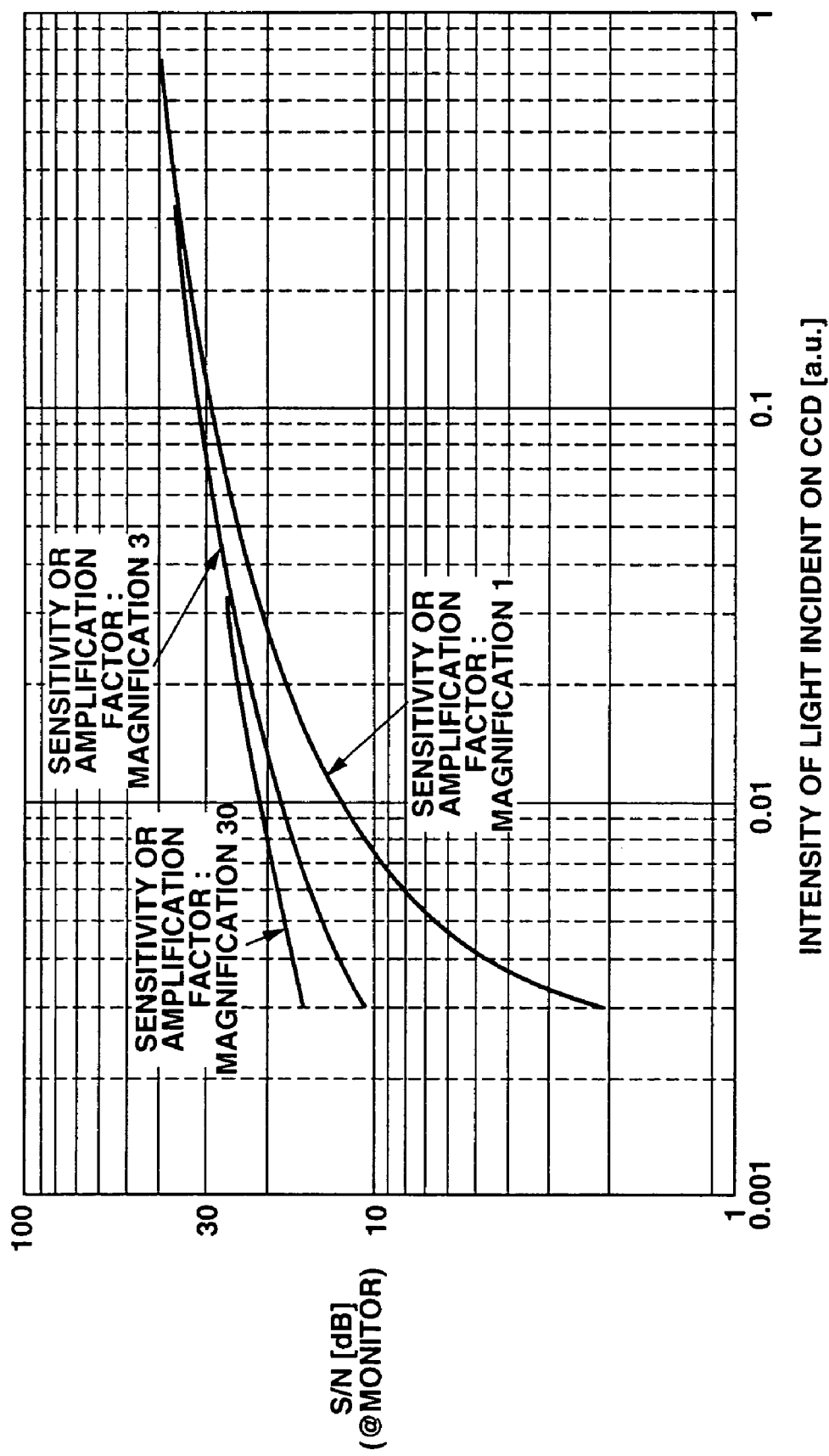

FIG. 7 or FIG. 8, shows the relationship between an output signal to be transmitted to the monitor 6, or between a signal-to-noise, and the intensity of light reflected from an object, which is established when a sensitivity or an amplification factor is varied by changing the voltage level (amplitude) of the sensitivity control pulse φCMD to be transferred to the charge multiplying detector 64.

As seen from the drawings, when the light reflected from an object is feeble (the intensity of light reflected from an object is low), if the sensitivity or amplification factor is set to 1 (no amplification), the brightness of an image on the monitor is low and the image quality (signal-to-noise ratio) thereof is low. As the sensitivity or amplification factor increases, the brightness of the image on the monitor increases and the image quality thereof gets higher.

The mode switching means 50 is a switch allowing an operator to freely select either of-observation modes, that is, either of the normal light mode and special light mode (fluorescence observation).

The mode switching means 50 may be located on the processor 3, light source unit 5, endoscope, 2 or all of them.

A mode switching signal sent from the mode switching means 50 is transmitted to each of the rotary filter switching means 46, RGB rotary filter control means 47, photometry means 37, CCD driving means 31, CCD sensitivity control means 32, and digital processing circuit 35.

Next, the light source unit 5 will be described below.

The lamp 40 emits illumination light which is constituted of a xenon lamp, a halogen lamp, an LED, an LD (semiconductor laser), or the like.

The condenser lens 45 concentrates illumination light, which is introduced from the lamp 40 via the diaphragm 41 and RGB rotary filter 43, on the back end of the light guide 12.

The diaphragm 41 and RGB rotary filter 43 are interposed between the lamp 40 and condenser lens 45. The RGB rotary filter 43 is coupled to the rotation shaft of the motor 44 such that it can be rotated, and controlled to rotate at a predetermined speed by the RGB rotary filter control means 47.

The RGB rotary filter control means 43 controls to a predetermined rotating speed the RGB rotary filter 43 (or the motor 44 that rotates the RGB rotary filter) according to the mode switching signal sent from the mode switching means 50. The RGB rotary filter control means 47 can make the rotating speed lower in the special light mode than in the normal light mode so as to extend an exposure period.

The diaphragm control means 42 receives an average of brightness values exhibited by a screen image from the photometry means 37, and compares the average of brightness values with an operator-designated target value of a brightness level of an image to be displayed on the monitor. An operator can freely designate the brightness of an image on the monitor using the brightness designating means 39 included in the light source unit 5.

Based on the result of the comparison (whether the average of brightness values is larger or smaller), the diaphragm control means 42 controls the opening or closing of the diaphragm 41 interposed between the lamp 40 and RGB rotary filter 43. Consequently, the diaphragm control means 42 controls an amount of light incident on the back end of the light guide 12.

Figure 9:
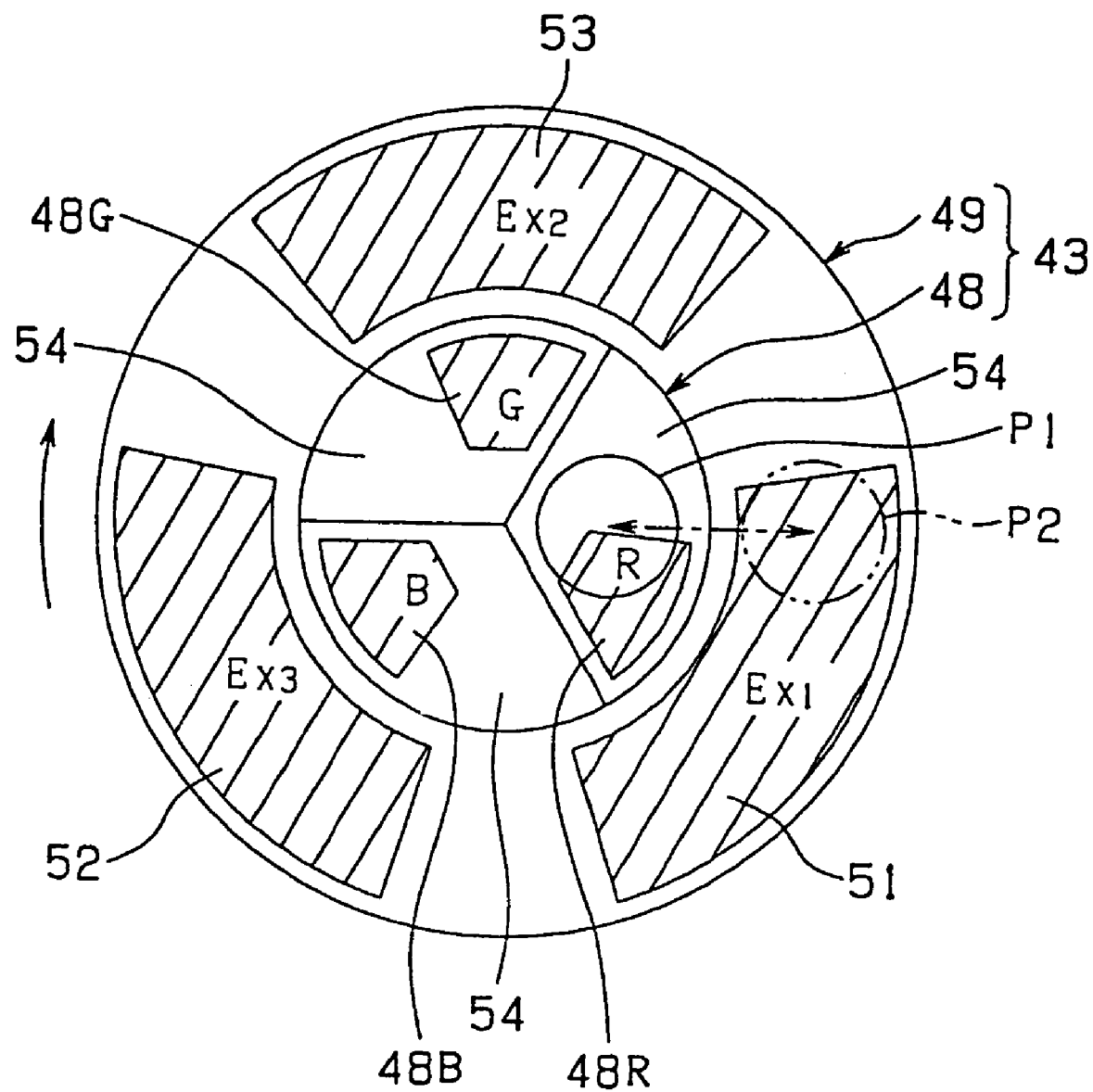

The RGB rotary filter 43 has, as shown in FIG. 9, a double structure including two filter sets 48 and 49 that serve as an inner circumference side thereof and an outer circumference side thereof.

As shown in FIG. 1, the rotary filter switching means 46 selectively moves either of the first filter set 48 that is the inner circumference side or the second filter set 49 that is the outer circumference side of the RGB rotary filter 43 shown in FIG. 7 on the optical axis of illumination light that links the lamp 40 and the back end of the light guide 12. In this case, the rotary filter switching means 46 moves the whole of the RGB rotary filter 43 and disposes the first filter set 48 that is the inner circumference side or the secondary filter set 49 that is the outer circumference side on the path of illumination light.

Specifically, in the normal light mode, the rotary filter switching means 46 disposes the filter set 48 in the inner circumference side on the path of illumination light emanating from the lamp 40. A light beam P1 (solid line in FIG. 9) emanating from the lamp 40 is introduced to the filter set 48 that is the inner circumference side.

In the special light mode, the rotary filter switching means 46 disposes the filter set 49 in the outer circumference side on the path of illumination light emanating from the lamp 40 (introduces a light beam P2 (dashed line in FIG. 9) emanating from the lamp 40 to the filter set 49 in the outer circumference side).

As shown in FIG. 9, the first filter set 48 in the inner circumference side of the RGB rotary filter 43 comprises three filters of red, green, and blue for the normal light mode, that is, filters 48R, 48G, and 48B that have the spectral characteristics of passing wavelength bands of the red (R), green (G), and blue (B) regions.

The second filter set 49 in the outer circumference side comprises three filters 51, 52, and 53 for three kinds of wavelength Ex1, Ex2, and Ex3 which have the spectral characteristics suitable for the special light mode (fluorescence observation).

For example, according to the present embodiment, the filter 51 for a wavelength Ex1 is an excitation light filter that passes light whose wavelengths range from 390 nm to 470 nm.

The filter 52 for a wavelength Ex2 is a reflected light filter having the property of passing light, of which wavelengths fall within a narrow band centered on 550 nm and are distributed to have a half width of about 10 nm, and the spectral characteristic with a transmittance of about several percents.

The filter 53 for a wavelength Ex3 is a reflected light filter having the property of passing light, of which wavelengths fall within a narrow band centered on about 600 nm and are distributed to have a half width of about 10 nm, and the spectral characteristic with a transmittance of about several percents.

Figure 10:
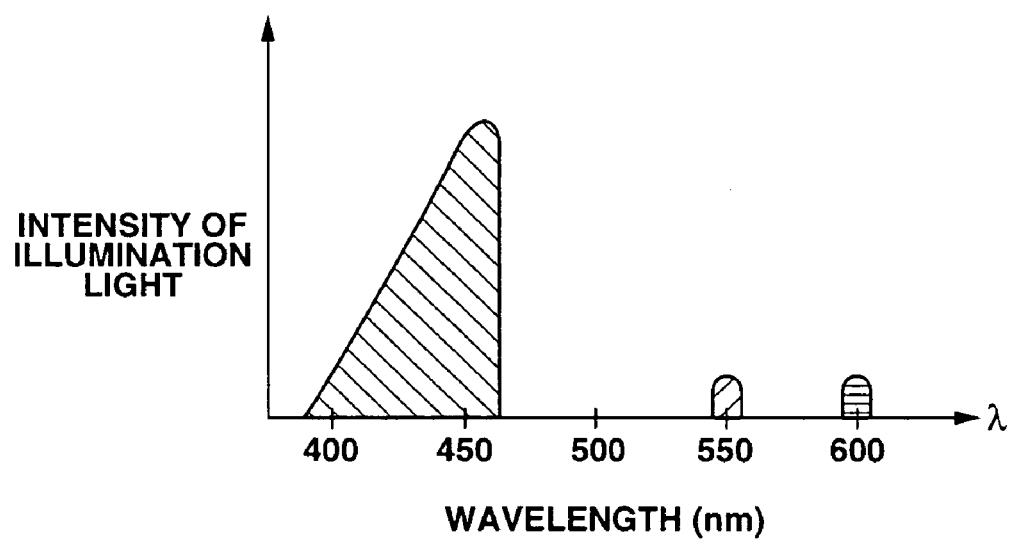

In the special light mode, illumination light irradiated through the illumination lens 16 incorporated in the endoscope 2 has a spectral characteristic like the one shown in, for example, FIG. 10.

The size of the filters 48R, 48G, and 48B is determined based on the exposure period during which the CCD 19 is exposed. The size of the interceptive part 54 formed between adjoining ones of the filters 48R, 48G, and 48B is determined based on the interception period during which the CCD 19 is intercepted (reading period). The same applies to the second filter set 49.

The circumferential length of the filters constituting the second filter set 49 for special light observation is larger than that of the filters constituting the first filter set 48 for normal light observation. This is because the exposure period is made longer for special light observation than for normal light observation.

Referring to FIG. 9, the normal light filters 48R, 48G, and 48B constitute the inner circumference side of the RGB rotary filter 43, and the special light filters 51, 52, and 53 constitute the outer circumference side thereof. Alternatively, the normal light filters 48R, 48G, and 48B may constitute the outer circumference side of the RGB rotary filter 43, and the special light filters 51, 52, and 53 may constitute the inner circumference side thereof.

According to the present embodiment, the memory 22 included in the storage device 20 serves as memory means in which a plurality of accumulation periods during which charges are accumulated in the CCD 19 is stored.

Moreover, the CCD driving means 31 serves as driving means for controlling the accumulation periods, during which charges are accumulated in the CCD 19 serving as a solid-state image pickup device, on the basis of the pieces of information on accumulation periods stored in the memory 22 included in the storage device 20.

The plurality of accumulation periods refer to accumulation periods during which charges are accumulated responsively to respective three kinds of wavelength in the normal light mode or special light mode.

(Operation)

The usage of the endoscope apparatus 1 in accordance with the first embodiment will be described below.

Figure 11A:
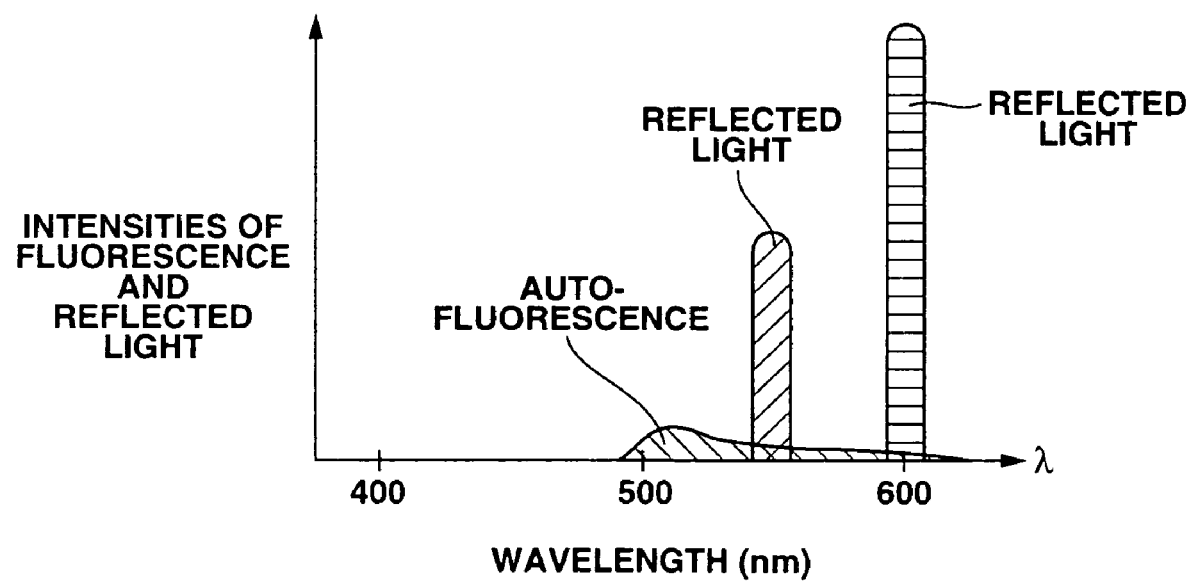
FIG. 11A is a graph indicating the spectral characteristics of fluorescence and reflected light employed in fluorescence observation.
Figure 11B:
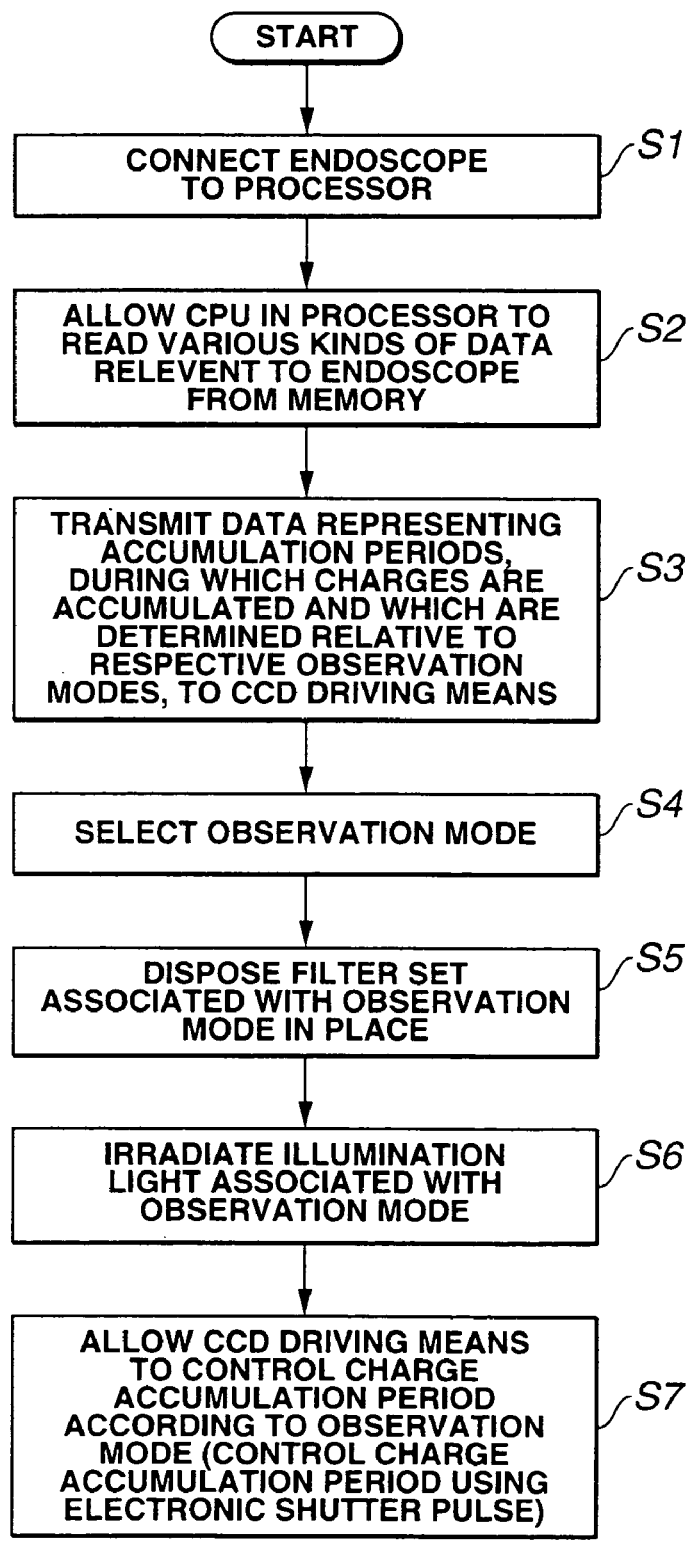

At the start of endoscopic examination, an operator connects the endoscope 2 to the processor 3 at step S1 described in FIG. 11B. The operator selects the endoscope 2 from among a plurality of types of endoscopes according a region to be observed, and connects the endoscope 2 to the processor 3.

Consequently, at step S2, the CPU 30 included in the processor 3 reads various kinds of data relevant to the endoscope 2 from the memory 22 included in the endoscope 2. Namely, the CPU 30 included in the processor 3 reads various kinds of data relevant to the endoscope 2 from the memory 22 in the storage device 20 incorporated in the endoscope 2 via the CPU 21 included in the storage device 20.

In this case, the data that represents the accumulation periods during which charges are accumulated in the CCD 19 responsively to respective three kinds of wavelength in the normal light mode or the special light mode (fluorescence observation) and which are associated with the type of endoscope, and that is one of the various kinds of data is read from the memory 22 into the CPU 30.

At step S3, the CPU 30 transmits the data, which represents the accumulation periods during which charges are accumulated in each of the observation modes (image pickup modes) and which is included in the various kinds of data, to the CCD driving means 31. Consequently, as described below, the CCD 19 is driven such that charges will be accumulated during appropriate accumulation periods in each of the observation modes.

Next, the operator manipulates the mode switching means 50 at step S4 so as to select an observation mode. Based on a directive signal indicating the selected observation mode, the filter set associated with the observation mode and included in the light source unit 5 is inserted into the path of illumination light at step S5. At step S6, illumination light associated with the observation mode is emitted from the light source unit 5 and irradiated to a region to be observed via the endoscope 2.

At step S7, the CCD driving means 31 controls the charge accumulation periods according to the observation mode. More specifically, the CCD driving means 31 uses an electronic shutter pulse φOFD, which is applied to the CCD 19, to control the charge accumulation periods.

The operation of the endoscope apparatus provided in each observation mode will be described below. The operations provided in the normal light mode and special light mode (fluorescence observation) will be described sequentially.

An operator inserts the insertional unit 11 of the endoscope 2 into a patient's body cavity (the bronchus, esophagus, stomach, large intestine, abdominal cavity, thoracic cavity, bladder, or womb) for the purpose of observation.

When normal light observation (normal light mode) is selected, the first filter set 58 of the rotary filter 43 is disposed on the path of illumination light, and the sensitivity or amplification factor offered by the CCD 19 is set to a amplification factor of 1 (no increase in sensitivity or no amplification). Illumination light emitted from the lamp 40 passes through the first filter set 48, whereby field-sequential illumination lights of red, green, and blue are irradiated time-sequentially to a living-body tissue, which is an object, through the illumination lens 16 by way of the light guide 12 included in the endoscope 2.

The CCD driving means 31 transmits the electronic shutter pulse φOFD during each of the exposure periods, during which the CCD 19 is exposed to each of reflected lights of red, green, and blue, according to the data that represents the accumulation periods during which charges are accumulated responsively to red, green, and blue lights in the normal light mode and that is received from the CPU 30. The CCD driving means 31 then controls the pulse duration of the electronic shutter pulse, during which charges are cleared, so as to establish desired accumulation periods.

The accumulation periods during which charges are accumulated at the pixel locations in the CCD 19 are shorter than those to be taken in a typical endoscope devoid of the sensitivity-valiable CCD 19. Light resulting from auto-fluorescence is so feeble that an amount of light incident on the light receiving surface of the CCD 19 must be increased. For example, the number of optical fibers constituting the light guide 12 is larger than that employed in the typical endoscope. The objective lens 17 is designed using a lens brighter than the one employed in the typical endoscope.

Therefore, during normal light observation, the intensity of light incident on the light receiving surface of the CCD 19 is larger than that employed in the general endoscope. Therefore, in order to adjust the magnitudes of signal charges, the accumulation periods are set to be short based on the type of endoscope.

The photometry means 37 calculates the level of a luminance signal that determines the average of brightness values exhibited by a screen image to be displayed on the monitor, and transmits the luminance signal to the diaphragm control means 42. The diaphragm control means 42 compares the luminance signal level with an operator-designated reference value (target value) of the brightness of an image to be displayed on the monitor. The diaphragm control means 42 controls the opening or closing of the diaphragm 41 according to the result of the comparison (whether the luminance signal level is higher or lower).

When the (luminance signal level) average of brightness values exhibited by a screen image to be displayed on the monitor is larger than the reference value, the diaphragm control means 42 causes the diaphragm 41 to move to close (so that the intensity of light introduced to the back end of the light guide 12 will get lower). On the other hand, when the average of brightness values exhibited by a screen image to be displayed on the monitor is lower than the reference value, the diaphragm control means 42 causes the diaphragm 41 to move to open (so that the intensity of light introduced to the back end of the light guide 12 will get higher).

As mentioned above, the endoscope apparatus 1 is designed to vary the intensity of illumination light to be irradiated to a living-body tissue so as to achieve automatic light adjustment (light adjustment by controlling the opening or closing of the diaphragm included in the light source unit 5). In the automatic light adjustment, the degree of opening of the diaphragm 41 is controlled such that the brightness of a screen image on the monitor 6 will be retained at the operator-designated value.

The lights of red, green, and blue reflected from a living-body tissue sequentially are incident on the CCD 19. A CCD output signal produced responsively to each of the reflected lights of red, green, and blue and sent from the CCD 19 is inputted to the signal processing unit 4. The analog processing circuit 33 and digital processing circuit 35 perform various kinds of signal processing on the CCD output signal, and transmit the resultant signal to the monitor 6 and peripheral equipment including image recording means alike. Consequently, a normal light image is displayed on the monitor 6 or recorded in the peripheral equipment.

The output signal sent to the monitor 6 exhibits the spectral characteristic shown in FIG. 7 corresponding to the sensitivity or amplification factor of 1, and exhibits the signal-to-noise ratio shown in FIG. 8 corresponding to the sensitivity or amplification factor of 1.

For fluorescence observation (special light mode), an operator manipulates a mode selection switch or the like serving as the mode switching means 50 disposed on the endoscope 2 or processor 3 so as to designate the special light mode (fluorescence observation). In response to the designation or directive, the rotary filter switching means 46 disposes the second filter set 49 included in the RGB rotary filter 43 on the path of illumination light. Moreover, the diaphragm control means 42 holds the diaphragm 41 in a nearly full open state because of the low intensity of light incident on the CCD 19.

When the endoscope 2 is approached to a living-body tissue for enlarged observation, the intensity of fluorescence incident on the CCD 19 gets higher. Even if the sensitivity or amplification factor offered by the charge multiplying detector 64 is set to 1 (no amplification), light representing an image to be displayed on the monitor may get saturated. In this case, the diaphragm control means 42 performs to control so as to close the diaphragm 41. Thus, an amount of light to be irradiated to an object is adjusted or controlled.

Illumination light emitted from the lamp 40 included in the light source unit 5 passes through the second filter set 49 included in the RGB rotary filter 43. At this time, blue band light is produced as excitation light through the filter Ex1, green narrow-band light is produced through the filter Ex2, and red narrow-band light is produced through the filter Ex3. These lights are incident on the back end (incident end surface) of the light guide 12 via the condenser lens 45. Subsequently, illumination light having the spectral characteristic (spectrum and intensity) shown, for example, in FIG. 10 is sequentially irradiated to a living-body tissue through the illumination lens 16 incorporated in the distal section 15 of the endoscope 2.

The CCD driving means 31 receives from the CPU 30 the data that represents the accumulation periods during which charges are accumulated responsively to fluorescence, green reflected light, and red reflected light respectively in the special light mode (fluorescence observation). When images of a fluorescence wavelength and two kinds of reflected light wavelength are picked up by the CCD 19, the CCD driving means 31 controls the pulse duration, during which charges are cleared, based on the received data. Thus, desired accumulation periods are established.

The accumulation period during which charges are accumulated responsively to a fluorescence wavelength is longer than the accumulation periods during which charges are accumulated responsively to two kinds of reflected light wavelength. The pulse duration is therefore made longer relative to the two kinds of reflected light wavelength than relative to the fluorescence.

The intensity of auto-fluorescence is much feebler than the intensity of reflected light. Moreover, the ratio of the intensities of a fluorescence wavelength and two kinds of reflective light wavelength varies depending on a region. When illumination light exhibiting the spectral characteristic shown in FIG. 10 is irradiated to a normal living-body tissue, an auto-fluorescence wavelength and two kinds of reflected light wavelength whose spectral characteristics are shown in FIG. 11A are produced at a region (one of a plurality of types of endoscopes) on the light receiving surface of the CCD 19.

Herein, assume that the ratio of the intensities of each wavelength, for example, the ratio of the intensity of fluorescence among green reflected (green narrow-band) light, and red reflected (red narrow-band) light is 1:5:10.

The accumulation periods TA during which charges are accumulated responsively to the respective lights, for example, fluorescence, green reflected light, and red reflected light in the special light mode shall be TE, 0.2*TE, and 0.1*TE respectively, and stored in the memory 22. Herein, * denotes a multiplication sign. When images of the fluorescence wavelength and two kinds of reflected light wavelength are picked up by the CCD during the respective accumulation periods, an average of brightness values exhibited by a screen image becomes nearly equal among the lights.

As mentioned above, an image of a fluorescence wavelength is picked up by the CCD during a longer accumulation period than the two kinds of reflected light wavelength are. Moreover, if the ratio of the intensities of the fluorescence and reflected light reflected from any other region becomes quite different, the CPU 30 takes the ratio of the intensities into consideration and calculates the accumulation periods during which charges are accumulated responsively to the fluorescence wavelength and two kinds of reflected light wavelength. Thus, the data representing the accumulation periods optimal to each of the types of endoscopes 2 is stored in the memory 22.

The photometry means 37 calculates an average of brightness values exhibited by a screen image to be displayed on the monitor, that is, a synthetic image produced from the fluorescence and reflected lights. The photometry means 37 transmits the result of the calculation to each of the CCD sensitivity control means 32 and diaphragm control means 42.

The CCD sensitivity control means 32 compares the average of brightness values exhibited by a screen image with an operator-designated reference (target) value of the brightness of an image to be displayed on the monitor. Based on the result of the comparison (whether the average of brightness values is larger or smaller), the CCD sensitivity control means 32 controls the voltage level (amplitude) of the sensitivity control pulse $\phi$CMD that is sent from the CCD driving means 31 to the CCD 19. The CCD sensitivity control means 32 thus controls the sensitivity or amplification factor to be offered by the charge multiplying detector 64 included in the CCD 19.

If the average of brightness values exhibited by a screen image on the monitor is larger than the reference value, the CCD sensitivity control means 32 lowers the voltage level of the sensitivity control pulse $\phi$CMD so as to decrease the sensitivity or amplification factor.

On the other hand, if the average of brightness values exhibited by a screen image on the monitor is smaller than the reference value, the CCD sensitivity control means 32 raises the voltage level (amplitude) of the sensitivity control pulse $\phi$CMD so as to increase the sensitivity or amplification factor.

Owing to the foregoing actions, automatic light adjustment is achieved by varying the sensitivity or amplification factor to be offered by the charge multiplying detector 64 included in the CCD 19 (AGC is achieved by controlling the sensitivity or amplification factor to be offered by the charge multiplying detector 64). Consequently, even when the brightness of an object varies, the brightness of a screen image displayed on the monitor 6 can be retained at the operator-designated value (target value).

Moreover, automatic light adjustment or control for varying the sensitivity or amplification factor to be offered by the charge multiplying detector 64 included in the CCD 19. Consequently, even when the sensitivity or amplification factor varies with a change in the temperature of the CCD, the brightness of a screen image displayed on the monitor 6 can be retained at the operator-designated value (target value).

Reflected light of excitation light irradiated to a living-body tissue and auto-fluorescence which results from fluorescence of the living-body tissue induced by the excitation light and whose peak wavelength-is about 520 nm is incident on the objective lens 17. The excitation light itself is cut out by the excitation light cut filter 18, and the auto-fluorescence alone is incident on the light receiving surface of the CCD 19. Moreover, the reflected light of the illumination light whose wavelengths fall within a green narrow band and a red narrow band is incident on the objective lens 17, passes through the excitation light cut filter 18, and is incident on the light receiving surface of the CCD 19.

Fluorescence, green reflected light, and red reflected light produced from the living-body tissue sequentially are incident on the CCD 19. A CCD output signal from the CCD 19 produces responsively to each of the three kinds of wavelength is inputted to the signal processing unit 4. The analog processing circuit 33 and digital processing circuit 35 perform various kinds of predetermined signal processing. Consequently, a fluorescence image is displayed on the monitor 6 or recorded in a personal computer or any other peripheral equipment.

Moreover, when images formed by fluorescence, green reflected light, and red reflected light are picked up by the CCD, the digital processing circuit 35 changes the values of white-balance coefficients to those that are set for the special light mode (fluorescence observation), that are different from those set for the normal light mode, and that are stored in the memory 22.

During color conversion, for example, the fluorescence is converted into a color signal of a green channel, the red reflected light is converted into a color signal of a blue channel, and the green reflected light is converted into a color signal of a red channel.

Consequently, an output signal sent to the monitor 6 exhibits the spectral characteristic shown in FIG. 7 corresponding to any sensitivity or amplification factor, and exhibits the signal-to-noise ratio shown in FIG. 8 corresponding to any sensitivity or amplification factor. In particular, when feeble light is concentrated on the CCD, the voltage level (amplitude) of the sensitivity control pulse φCMD to be applied to the charge multiplying detector 64 included in the CCD 19 is changed in order to increase the sensitivity or amplification factor. Consequently, an output signal that exhibits the spectral characteristic or signal-to-noise ratio relevant to a sensitivity or amplification factor of a magnification of 3 or 10 is transmitted to the monitor 6. Incidentally, the sensitivity or amplification factor is not limited to 3 and 10 but may be set to any value by controlling the voltage level (amplitude) of the sensitivity control pulse ACED.

Fluorescence observation utilizes the characteristic that: for example, when excitation light whose wavelengths fall within the blue region is irradiated to the mucosa, auto-fluorescence whose peak wavelength is about 520 nm is produced; and the intensity of auto-fluorescence produced at a lesion is smaller than that produced at a normal region.

Moreover, green reflected light that is adopted can sharply reflect the influence of blood, that is, hemoglobin absorption band relative to hemoglobin. Moreover, red reflected light is adopted as reference light (light unaffected by blood). In this case, a synthetic image produced by picking up the image of a region that is an object of observation is an image from which the presence or absence of a lesion can be sharply detected with the influence of inflammation (blood) removed.

For example, during fluorescence observation, inflammation or hyperplasia is visualized in the same color as a normal tissue is, but an adenoma or a carcinoma is visualized in a color different from the color in which the normal tissue is visualized. Consequently, a tumorous lesion can be detected more easily during fluorescence observation than it is during normal light observation.

(Advantage)

According to the first embodiment, advantages described below are provided.

According to the present embodiment, various kinds of data relevant to the endoscope 2 are stored in the memory 22 included in the storage device 20. Consequently, observation can be achieved based-on information optimal for a selected type of endoscope (a region to be observed).

Moreover, according to the present embodiment, since stored data is read and used for control, a control sequence is simple. In the special light mode (for example, fluorescence observation), images formed by a fluorescence and reflected lights whose intensities are largely different from one another are picked up. In this case, the accumulation period during which charges are accumulated is controlled responsively to vary depending on the wavelength. Consequently, each of images produced from the fluorescence and reflected lights respectively can be picked up with appropriate brightness.

Moreover, according to the present invention, a synthetic image can be produced using a fluorescence and reflected lights. In this case, a fluorescence observation image is determined with appropriate brightness. Thus, image quality good enough for diagnosis can be ensured.

Second Embodiment

Figure 12:
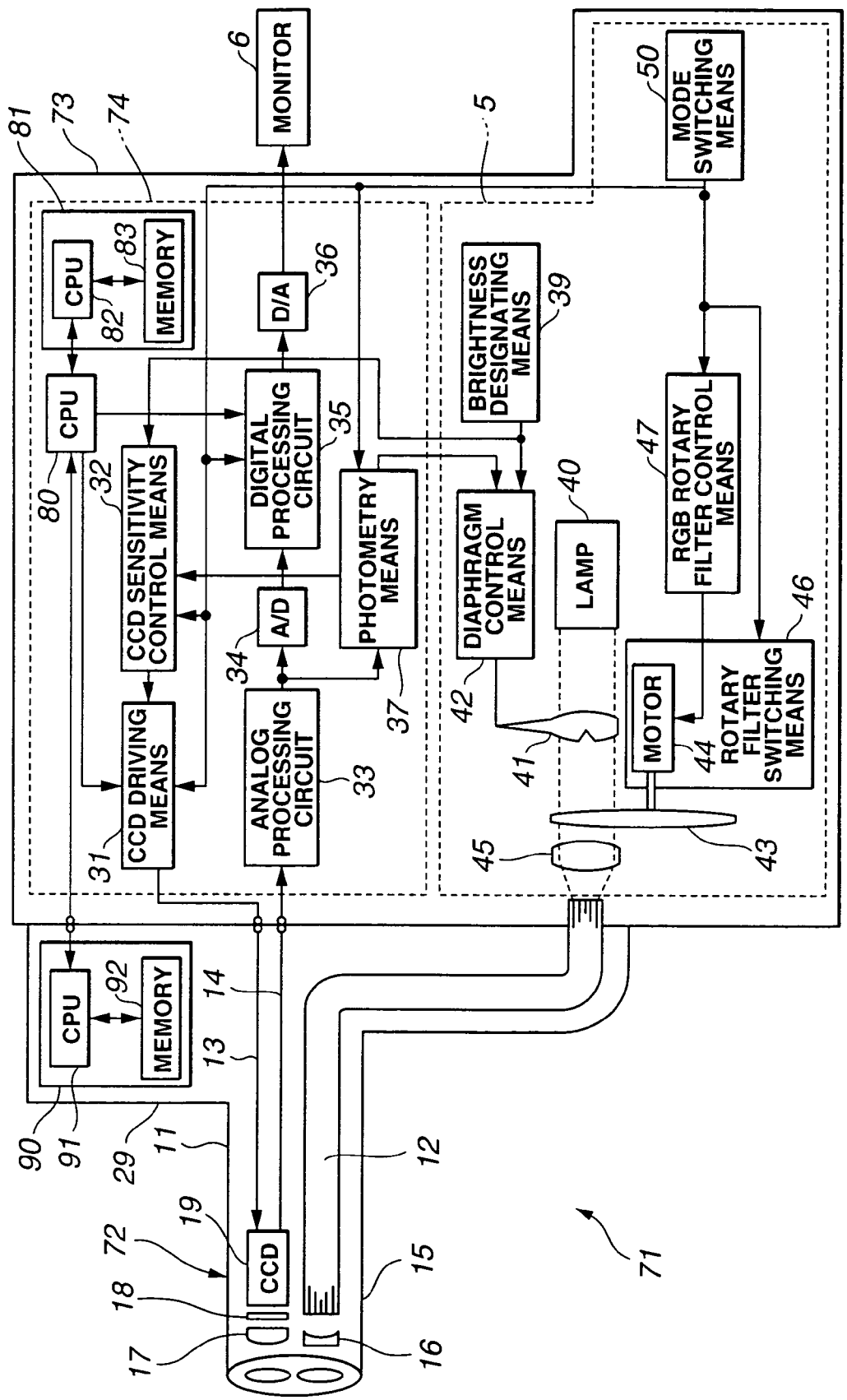
FIG. 12 is a block diagram schematically showing the configuration of an endoscope apparatus in accordance with a second embodiment of the present invention.

FIG. 12 is a block diagram schematically showing the configuration of an endoscope apparatus in accordance with a second embodiment of the present invention. The same reference numerals will be assigned to components identical to those of the first embodiment described in conjunction with FIG. 1 to FIG. 11B, and the description of the components will be omitted.

(Configuration)

In the first embodiment shown in FIG. 1 to FIG. 11B, the memory means in which the data representing the accumulation periods, during which charges are accumulated responsively to each wavelength and which are different among a plurality of types of endoscopes, is stored is incorporated in the endoscope. In an endoscope apparatus 71 in accordance with the present embodiment, the memory means in which the data representing the accumulation periods is stored is incorporated in a processor 73.

A storage device 81 is incorporated in a signal processing unit 74 included in the processor 73.

According to the present embodiment, the storage device 81 comprises a CPU 82 and a memory (EEPROM) 83 serving as memory means.

The memory 83 is a nonvolatile memory in which data is stored.

The CPU 82 controls reading or writing of data from or to the memory 83, and controls transmission or reception (communication) of data to or from a CPU 80 included in the processor 73.

In the memory 83, the accumulation periods (electronic shutter speeds) during which charges are accumulated responsively to three kinds of wavelength of red, green, and blue in a normal light mode are stored. Moreover, the accumulation periods (electronic shutter speeds) during which charges are accumulated responsively to three kinds of wavelength of fluorescence Ex1, green reflected light Ex2, and red reflected light Ex3 in a special light mode (fluorescence observation) are stored in the memory 83.

Instead of the accumulation periods, a charge clear period or the ratio of the accumulation periods during which charges are accumulated responsively to three kinds of wavelength may be stored in the memory 83.

The accumulation period during which charges are accumulated responsively to a fluorescence wavelength is made longer than the accumulation periods during which charges are accumulated responsively to two kinds of reflected light wavelength.

The accumulation periods during which charges are accumulated responsively to three kinds of wavelength of red, green, and blue in the normal light mode and which are stored in the memory 83 are shorter than those determined when a typical CCD that is different from a sensitivity-variable CCD such as the CCD 19 is incorporated in an endoscope.

The accumulation periods during which charges are accumulated responsively to three kinds of wavelength that are different between the normal light mode and special light mode (fluorescence observation) and which are stored in the memory 83 are determined optimally for a plurality of types of endoscopes (for examination of the bronchus, superior alimentary tract, inferior alimentary tract, and cranio-cervix). Data items representing the accumulation periods determined for the plurality of types of endoscopes are stored in the memory 83.

A storage device 90 is incorporated in an endoscope 72.

The storage device 90 comprises a CPU 91 and a memory (EEPROM) 92. The memory 92 is a nonvolatile memory in which data is stored.

The CPU 91 controls reading or writing of data from or to the memory 92, and controls transmission or reception (communication) of data to or from the CPU 80 incorporated in the processor 73.

Moreover, an endoscope model (type) name, an endoscope serial number, white-balance set values (for normal light and for special light (fluorescence observation)), the number of times by which the endoscope is connected to the processor and the power supply of the endoscope is turned on, information on a forceps channel included in the endoscope, the outer diameter of the distal section of the endoscope, the outer diameter of the insertional unit of the endoscope, and the like are stored in the memory 92.

The CPU 80 is incorporated in the signal processing unit 74. The CPU 80 controls via the CPU 91 reading of various kinds of data relevant to the endoscope from the memory 92. Moreover, the CPU 80 controls via the CPU 82 a reading of the accumulation periods, during which charges are accumulated responsively to three kinds of wavelength in the normal light mode or special light mode (fluorescence observation), from the memory 83.

The CPU 80 judges the type of endoscope connected to the processor 73 from various kinds of data read from the memory 92 (whether the endoscope is dedicated for examination of the bronchus, superior alimentary tract, inferior alimentary tract, or cranio-cervix). The CPU 80 reads the data, which represents the accumulation periods, during which charges are accumulated responsively to three kinds of wavelength in the normal light mode or special light mode (fluorescence observation) corresponding to the type of endoscope employed, from the memory 83, and transmits the data to the CCD driving means 31.

Moreover, the endoscope model name, serial number, and white-balance set values (for normal light and for special light) read from the memory 92 are transmitted to the digital processing circuit 35.

Consequently, when the endoscope 72 is connected to the processor 73, various kinds of data stored in the memory 92 are read into the CPU 80 via the CPU 91. Moreover, the data representing the accumulation periods and being stored in the memory 83 is read into the CPU 80 via the CPU 82.

(Operation)

The usage of the endoscope apparatus 71 in accordance with the second embodiment will be described below.

At the start of endoscopic examination, an operator selects the endoscope 72 according to a region to be observed from among a plurality of types of endoscopes and connects the endoscope 72 to the processor 73. The CPU 80 included in the processor 73 reads various kinds of data relevant to the endoscope 72 from the memory 92 via the CPU 91 included in the storage device 90 incorporated in the endoscope 72.

The CPU 80 judges the type of endoscope 72 connected to the processor 73 from the various kinds of data read from the memory 92 (whether the endoscope is dedicated to examination of the bronchus, superior alimentary tract, inferior alimentary tract, or cranio-cervix). The CPU 80 reads the data, which represents the accumulation periods during which charges are accumulated responsively to three kinds of wavelength in the normal light mode or special light mode (fluorescence observation) corresponding to the type of endoscope 72, from the memory 83, and transmits the read data to the CCD driving means 81. The CCD driving means 31 drives and controls the CCD 19 in response to a mode switching signal sent from the mode switching means 50.

(Advantages)

The present embodiment provides advantages described below.

According to the present embodiment, in the special light mode (fluorescence observation), images formed by a fluorescence and reflected-lights whose intensities are largely different from one another are picked up. Nevertheless, since the accumulation period during which charges are accumulated is different from light to light, images produced from the fluorescence wavelength and two kinds of reflected light wavelength respectively are formed with appropriate brightness. Moreover, according to the present embodiment, a synthetic image produced by synthesizing the images, that is, a fluorescence observation image exhibits appropriate brightness and enjoys high image quality.

According to the present embodiment, the data representing the accumulation periods determined for the normal light mode and special light mode (fluorescence observation) respectively is stored in the memory means incorporated in the processor. The storage capacity of the memory means incorporated in the endoscope 72 can be reduced accordingly.

Third Embodiment

Figure 13:
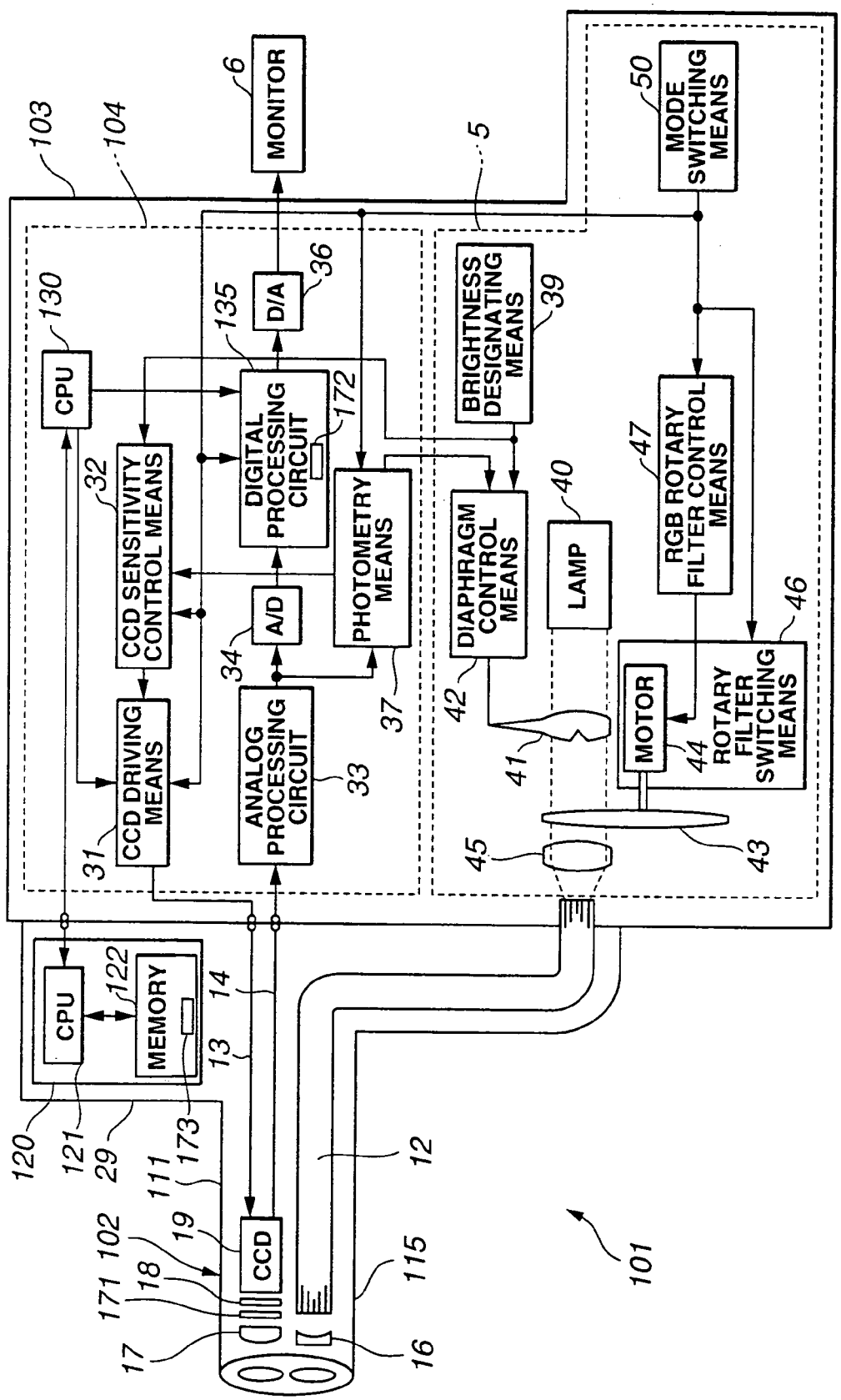
FIG. 13 is a block diagram schematically showing the configuration of an endoscope apparatus in accordance with a third embodiment of the present invention.

FIG. 13 is a block diagram schematically showing the configuration of an endoscope apparatus in accordance with a third embodiment of the present invention. The same reference numerals will be assigned to components identical to those of the first embodiment shown in FIG. 1 to FIG. 11B, and the description of the components will be omitted.

As shown in FIG. 13, an endoscope apparatus 101 in accordance with a third embodiment comprises, in addition to the same components as those included in the first embodiment shown in FIG. 1 to FIG. 11B, spatial frequency characteristic converting means (pupil modulation element) and spatial frequency characteristic restoring means. Owing to these additional components, as described below, even when a lens offering a large aperture ratio is employed as a member of an optical system including the objective lens 17 through which an optical image is formed on the CCD 19, a decrease in a depth of field can be prevented. Eventually, an image enjoying a high signal-to-noise ratio can be produced.

Specifically, an optical member is included for modifying an optical property of an optical system, which forms images on the CCD 19, through modulation. An output signal of the CCD 19 is electrically corrected by performing restoration optimally corresponding to the optical member. This results in an image enjoying a higher signal-to-noise ratio.

Spatial frequency characteristic converting means 171 for converting a spatial frequency characteristic is interposed between the objective lens 17 and the excitation light cut filter 18 incorporated in a distal section 115 of an insertional unit 111 incorporated in the endoscope apparatus 101.

The spatial frequency characteristic converting means 171 and spatial frequency characteristic restoring means 172, which are incorporated in the endoscope apparatus 101 and will be described later, realize the technology described in, for example, Japanese Unexamined Patent Application Publication No. 2000-5127.

The spatial frequency characteristic converting means 171 is constituted of a pupil modulation element. Assume that a Z denotes the optical axis of the optical system, an A denotes an axis orthogonal to the Z axis and parallel to the horizontal direction of an array of pixel locations in a solid-state image-pickup device (horizontal direction of a monitor), and a Y denotes an axis is orthogonal to the Z axis and parallel to the vertical direction of the array of the pixel locations in the solid-state image-pickup device (vertical direction of the monitor). The optical element or optical member has the surface thereof three-dimensionally curved under the condition of $Z=A(X^3+Y^3)$. This is based on the property of a rotationally asymmetric optical element of causing a rotationally asymmetric blur (rotationally asymmetric aberration). According to the present embodiment, despite the objective lens 17 is a lens offering a large aperture ratio (that is, a smaller f-number) and forming a bright image, a small depth of field can be adopted in the objective lens 17.

Spatial frequency characteristic restoration data 173 is stored in the memory 122 incorporated in the endoscope 102 having the spatial frequency characteristic converting means 171.

Incidentally, the directions in which the pixel locations in the CCD 19 are arrayed may not agree with the directions (X and Y directions) of the pupil modulation element. Moreover, the shape of the pupil modulation element is not limited to any specific one.

A digital processing circuit 135 is identical to the digital processing circuit 35 employed in the first embodiment except that the digital processing circuit 135 includes the spatial frequency characteristic restoring means 172.

The spatial frequency characteristic converting means 171 has the characteristic of a rotationally asymmetric optical element of causing a rotationally asymmetric blur (rotationally asymmetric aberration). The spatial frequency. characteristic restoring means 172 is means for correcting the blur by performing electric signal processing. The spatial frequency characteristic restoring means 172 is realized with, for example, a spatial filter having asymmetric numerals specified therein as filtering coefficients by which peripheral pixels of each pixel are weighted.

The filtering coefficient shall be a value determined with the degree of blur which is a rotationally asymmetric aberration or blur caused by the spatial frequency characteristic converting means 171. If the degree of a blur is small, the filtering coefficients may be symmetric numerals.

The spatial frequency characteristic restoring means 172 performs arithmetic or logic operations only when the spatial frequency characteristic restoration data 173 is stored in the memory 122.

A storage device 120 comprises a CPU 121 and a nonvolatile memory 122.

The memory 122 is realized with a nonvolatile EEPROM or the like. The spatial frequency characteristic restoration data 173 including the filtering coefficients used to restore a spatial frequency characteristic is stored in the memory 122.

The CPU 121 controls reading or writing of data from or to the memory 122, and also controls transmission or reception (communication) of data to or from the processor 3.

A CPU 130 reads the spatial frequency characteristic restoration data 173 from the memory 122 via the CPU 121, and transmits the read data to the digital processing circuit 135.

According to the present embodiment, the spatial frequency characteristic converting means 171 is an optical member having the surface thereof rotationally symmetric to the surface of a solid-state image-pickup device that captures an object image.

The memory 122 included in the storage device 120 is memory means in which restoration data used to restore a change in optical performance caused by the optical member is stored.

(Operation)

The usage of the endoscope apparatus 101 in accordance with the third embodiment will be described below.

At the start of endoscopic examination, an operator selects the endoscope 102 from among a plurality of types of endoscopes corresponding to a region, and connects the endoscope 102 to the processor 103. The CPU 130 included in the processor 103 reads various kinds of data relevant to the-endoscope 102 from the memory 122 via the CPU 121 included in the storage device 120 incorporated in the endoscope 102. Spatial frequency characteristic restoration data items (filtering coefficients) associated with the plurality of types of endoscopes, which are one of various kinds of data, are also read from the memory 122 into the CPU 130, and then transmitted to the digital processing circuit 135.

During normal light observation, lights of red, green, and blue reflected from a living-body tissue sequentially are incident on the CCD 19 via the objective lens 17, spatial frequency characteristic converting means 171, and excitation light cut filter 18. During fluorescence observation, fluorescence, green reflected light, and red reflected light produced by a living-body tissue sequentially are incident on the CCD 19 via the same optical members. A CCD output signal produced responsively to each wavelength is transmitted to the signal processing unit 104.

When the spatial frequency characteristic converting means 171 is included, compared with when the spatial frequency characteristic converting means 171 is not included, an image signal to be sent to the signal processing unit 104 represents a blurred image.

The spatial frequency characteristic restoring means 172 included in the digital processing circuit 135 incorporated in the signal processing unit 104 uses the spatial frequency characteristic restoration data read from the memory 122 via CPU 130 to perform spatial filtering. Specifically, peripheral pixels of each pixel are multiplied by filtering coefficients for use in restoring a spatial frequency characteristic. Consequently, an image blurred due to the presence of the spatial frequency characteristic converting means 171 is restored. In addition, other predetermined signal processing is performed. Eventually, a normal light image is displayed or recorded on the monitor 6 or peripheral equipment such as a personal computer.

(Advantages)

The present embodiment provides advantages described below.

According to the present embodiment, the same advantages as those of the first embodiment are provided. In addition, since the spatial frequency characteristic converting means 171 is included, while a conventional depth of field is retained, an f-number of an objective lens included in the optical system can be decreased (a bright lens can be adopted).

Consequently, according to the present invention, even when the intensity of light reflected from an object is unchanged, the intensity of light incident on the CCD can be increased. In particular, when feeble light is incident on the CCD, high image quality supported by a high signal-to-noise ratio can be provided.

According to the first to third embodiments, the accumulation periods determined for the normal light mode and special light mode (fluorescence observation) respectively may be stored in the memory means incorporated in the processor. The spatial frequency characteristic restoration data 173 may be stored in the memory means incorporated in the endoscope.

According to the first to third embodiments, the CCD 19 including the facility for varying the sensitivity thereof is adopted as an image sensor. Alternatively, a typical CCD, a rear-side incidence CCD, a CMOS image sensor, or the like may be adopted. Otherwise, an avalanche photodiode device (APD) type image sensor constituting pixels or a horizontal register with avalanche photodiodes may be disposed.

The charge multiplying detector may be disposed at each pixel location. In this case, charge amplification is enabled with application of a sensitivity control pulse from the processor to each of the charge multiplying detectors included in the CCD. The sensitivity or amplification factor can be adjusted by controlling the voltage level (amplitude) of the sensitivity control pulse or the number of sensitivity control pulses.

According to the first to third embodiments, a CCD serving as a solid-state image-pickup device is incorporated in the distal section of an endoscope. Alternatively, two CCDs may be incorporated in the distal section of an endoscope. The first CCD may be used exclusively for the normal light mode and the second CCD may be used exclusively for the special light mode.

In this case, CCD switching means formed with a relay or the like and used to produce a CCD driving signal and a reading signal may be incorporated in an endoscope or may be contained in a cable that links the endoscope and the processor. The CCD associated with each observation mode may be driven or read according to a mode switching signal sent from the mode switching means. Moreover, CCD driving/reading circuits associated with the two CCDs may be incorporated in the processor.

According to the first to third embodiments, three kinds of wavelength employed in the special light mode are fluorescence, green reflected light, and red reflected light. The wavelength of excitation light or reflected light, selection or combination of the center wavelength thereof and the wavelength band thereof can be determined arbitrarily.

According to the first to third embodiments, special wavelength employed in the special light mode are an auto-fluorescence and reflected light. The present invention is not limited to this combination. Alternatively, the combination of a light caused by chemifluorescence and reflected lights will do. Moreover, the combination of a plural kinds of reflected light wavelength will do. In this case, the wavelength of excitation light or reflected light, selection or combination of the wavelength band and the like thereof can be determined arbitrarily.

According to the first to third embodiments, the CCD is incorporated in the distal section of the endoscope. Alternatively, the CCD may be incorporated outside a fiberscope that has an image optical fiber bundle by which an optical image is transmitted within the endoscope (any place other than an insertional unit). Namely, a hybrid structure having the CCD integrated thereto will do. Otherwise, the CCD may be integrated into the endoscope but may be freely detachable or attachable from or to the endoscope. Namely, non-hybrid structure having the CCD integrated thereto will do.

According to the first to third embodiments, a sensitivity-valiable CCD is used to pick up images formed by feeble auto-fluorescence. In order to pick up images formed by the auto-fluorescence at a higher signal-to-noise ratio, a pixel binning reading technique or the like for adding up peripheral pixels of each pixel in the CCD may be adopted in combination.

Fourth Embodiment

Referring to FIG. 14 to FIG. 18, a fourth embodiment of the present invention will be described below.

In description of the fourth embodiment of, the present invention using FIG. 14 to FIG. 18, the same reference numerals will be assigned to components identical to those of the first embodiment shown in FIG. 1 to FIG. 11B. The description of the components will be omitted.

(Configuration)

Figure 14:
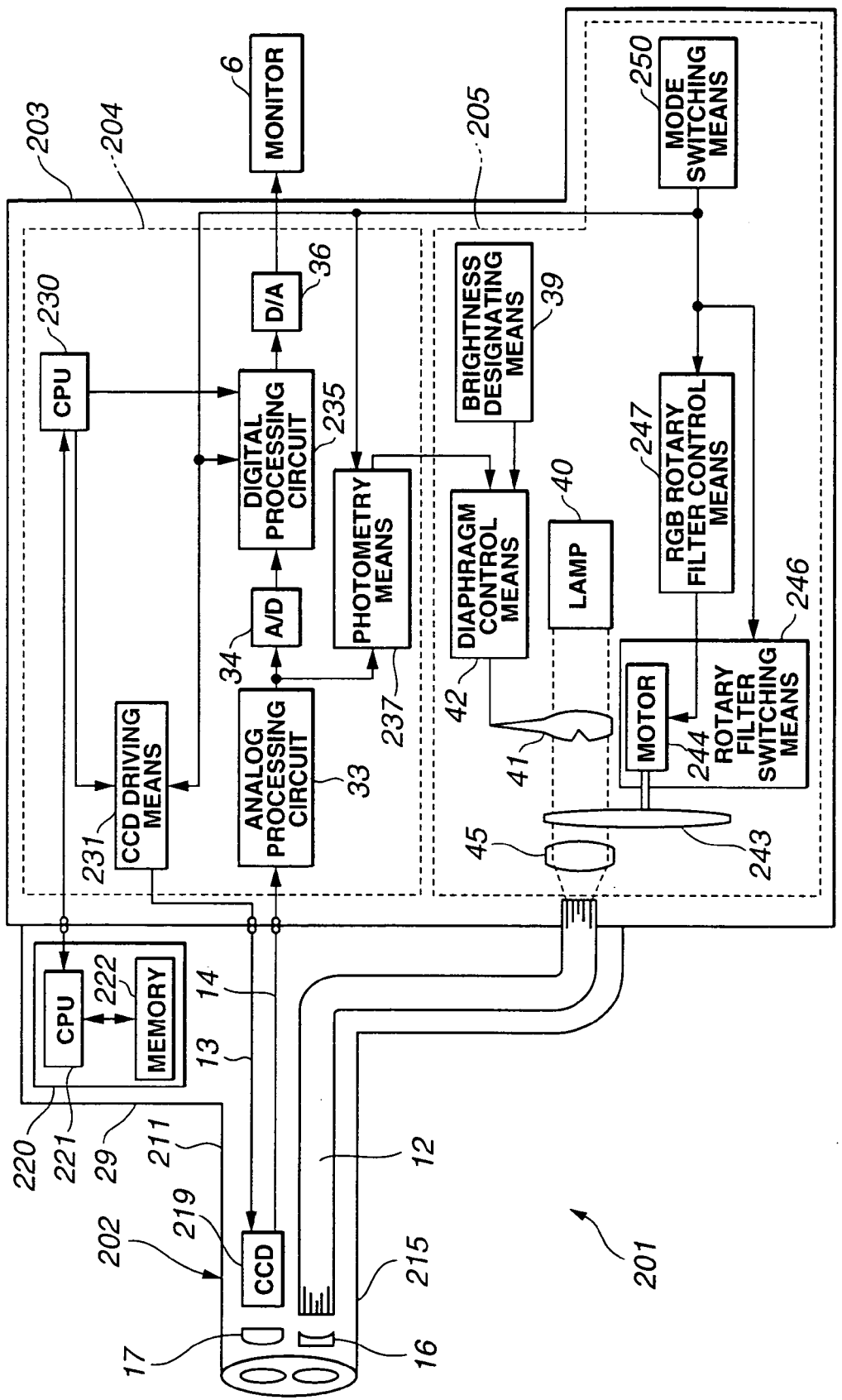
FIG. 14 to FIG. 18 are concerned with a fourth embodiment of the present invention.
Figure 15:
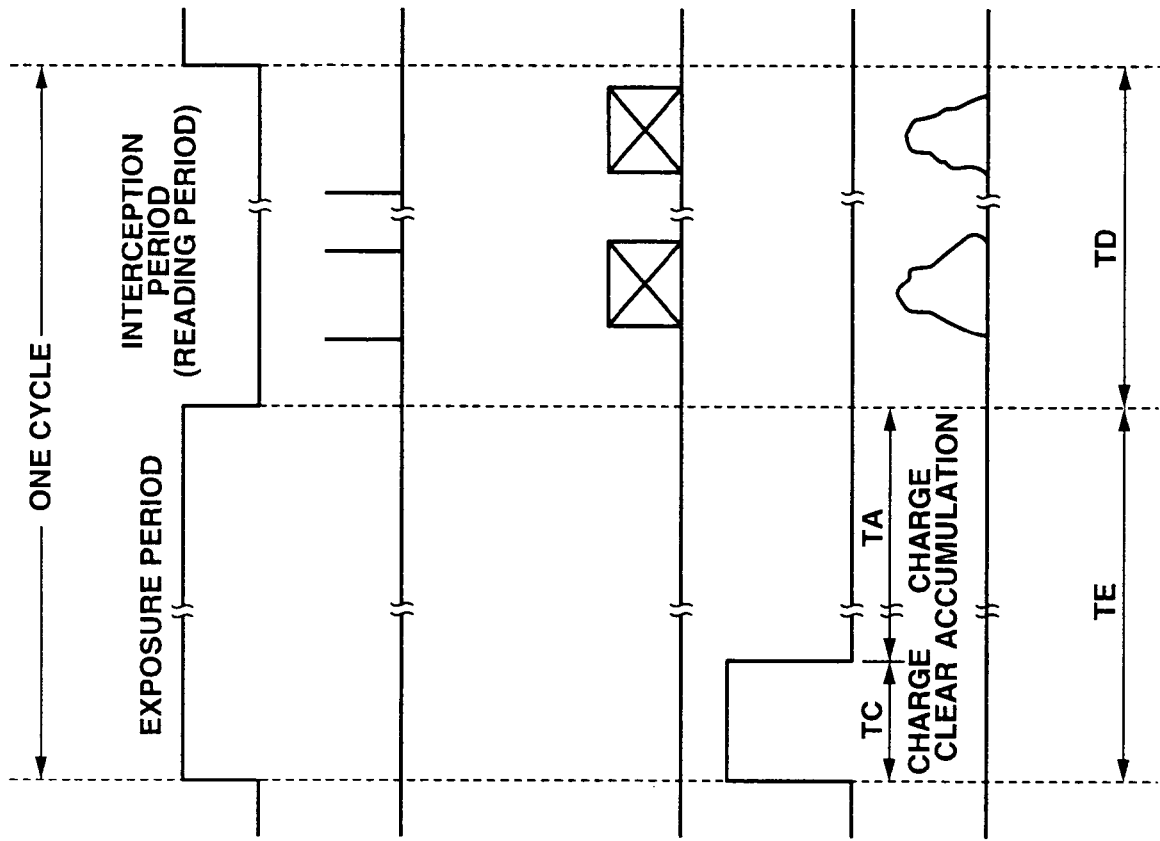

As shown in FIG. 14, an endoscope apparatus 201 in accordance with the fourth embodiment is designed to enable nar-row-band light observation as observation in a special light mode, and comprises an endoscope 202, a processor 203, and the monitor 6.

The endoscope 202 has an elongated insertional unit 211 that is inserted into a patient's body cavity.

The light guide 12, the plurality of CCD driving signal lines 13, and the plurality of CCD output signal lines 14 lie through the insertional unit 211.

The distal part of the light guide 2, an illumination lens 16, the objective lens 17, and a CCD 219 are incorporated in a distal section 215 of the insertional unit 211. Namely, no excitation light cut filter is incorporated in a distal section 215.

Over the light guide 12, illumination light emanating from a light source unit 205 incorporated in the processor 203 is introduced to the distal section 215 of the insertional unit 211.

An image is formed by light returned from an object on the light receiving surface of the CCD 219 via the objective lens 17.

The CCD 219 is incorporated in the distal section 215 of the insertional unit 211, and serves as an image sensor disposed at the position of the image plane of the objective lens 17. Referring to FIG. 14, the optical elements are arranged in order to realize a direct-vision type endoscope. Alternatively, the optical elements may be arranged in order to realize an oblique-vision or side-vision type endoscope.

Moreover, the CCD 219 is connected to CCD driving means 231 incorporated in a signal processing unit 204 included in the processor 203. The CCD 219 is driven with a driving signal produced by the CCD driving means 231. In response to the driving signal, an electronic shutter is controlled by the CCD 219 and signal charges are accumulated in the CCD 219.

An object image formed on the light receiving surface of the CCD 219 via the objective lens 17 is photoelectrically converted pixel by pixel in the CCD 219, and then transmitted.

An output signal of the CCD 219 is transmitted to an analog processing circuit 33 incorporated in the signal processing unit 204 included in the processor 203 via the CCD output signal lines 14.

A storage device 220 is incorporated in-the endoscope 202. The storage device 220 comprises a CPU 221 and a nonvolatile memory 222.

The memory 222 is an EEPROM or the like and nonvolatile. Data is stored in the memory 222.

The CPU 221 controls reading or writing of data from or to the memory 222, and also controls transmission or reception (communication) of data to or from the processor 203.

The accumulation periods (electronic shutter speeds) during which charges are accumulated responsively to three kinds of wavelength of red, green, and blue in a normal light mode are stored in the memory 222. Moreover, the accumulation periods (electronic shutter speeds) during which charges are accumulated responsively to three kinds of wavelength Ex1, Ex2, and Ex3 in a special light mode (narrow-band light observation) are stored in the memory 222. Instead of the accumulation periods, a charge clear period or the ratio of the accumulation periods during which charges are accumulated responsively to three kinds of wavelength may be stored in the memory 222.

The accumulation periods during which charges are accumulated responsively to three kinds of wavelength in the special light mode and which are stored in the memory 222 are determined optimally corresponding to each of a plurality of types of endoscopes (for examination of the bronchus, superior alimentary tract, inferior alimentary tract, craniocervix, and bladder). The accumulation period during which charges are accumulated responsively to blue narrow-band light is longer than that during which charges are accumulated responsively to green or red narrow-band light.

The accumulation periods during which charges are accumulated responsively to three kinds of wavelength in the normal light mode and which are stored in the memory 222 are shorter than those determined for a typical endoscope designed for normal light observation.

Aside from the data representing the accumulation periods, data relevant to the endoscope is stored in the memory 222.

Namely, an endoscope model (type) name, an endoscope serial number, white-balance set values (for normal light and for special light (narrow-band light observation)), the number of times by which the endoscope is connected to the processor and the power supply of the endoscope is turned on, information on a forceps channel included in the endoscope, the outer diameter of the distal section of the endoscope, and the outer diameter of the insertional unit of the endoscope are stored in the memory 22.

The signal processing unit 204 comprises a CPU 230, CCD driving means 231, the analog processing circuit 33, the A/D converter 34, a digital processing circuit 235, the D/A converter 36, and a photometry means 237.

The light source unit 205 comprises the lamp 40, the diaphragm 41, the diaphragm control means 42, an RGB rotary filter 243, a motor 244, the condenser lens 45, a rotary filter switching means 246, an RGB rotary filter control means 247, and a mode switching means 250.

The CPU 230 is incorporated in the signal processing unit 204.

When the endoscope 202 is connected to the processor 203, the CPU 230 controls reading of various kinds of data from the memory 222 via the CPU 221. In this case, the various kinds of data stored in the memory 222 are transmitted to the CPU 230 via the CPU 221. Namely, the CPU 230 reads various kinds of data from the memory 222.

Moreover, the CPU 230 transmits the data, which represents the accumulation periods during which charges are accumulated responsively to three kinds of wavelength in the normal light mode or special light mode (narrow-band observation) and which are read from the memory 22, to the CCD driving means 231. Moreover, the CPU 230 transmits the endoscope model name, serial number, and white-balance set values (for normal light and for special light) to the digital processing circuit 235.

FIG. 15A to FIG. 15E show the timings of driving signals to be applied to the CCD 219 responsively to one of three kinds of wavelength and the timing of an output signal of the CCD 219. Specifically, FIG. 15A indicates the action of the RGB rotary filter 243, and FIG. 15B indicates the timing of vertical transfer pulses φP1 and φP2. FIG. 15C indicates the timing of horizontal transfer pulses φS1 and φS2, and FIG. 15D indicates the timing of an electronic shutter pulse φOFD. FIG. 15E indicates the timing of the output signal of the CCD 219.

Referring to FIG. 15A to FIG. 15E, TE denotes an exposure period. During the exposure period TE, signal charges are accumulated in the CCD 219 proportionally to the intensity of light reflected from an object and incident on the light receiving surface of the CCD 219.

During a period TD, signal charges accumulated during the period TE are transferred to a horizontal transfer register in response to the vertical transfer pulses φP1 and φP2 in units of signal charges juxtaposed on one horizontal line. The charges are then sequentially transferred to a floating diffusion amplifier included in the CCD 219 in response to the horizontal transfer pulses φS1 and φS2. The floating diffusion amplifier converts the charges into voltages, and transmits the voltages as an output signal indicated in FIG. 15E.

The electronic shutter pulse φOFD indicated in FIG. 15D can be transmitted with any pulse duration or by any number of pulses during the period from the start of the exposure period and the end thereof (start of an interception period). Charges accumulated in the respective pixel locations are released to a substrate.

During the period TE, object image data can be accumulated in light receivers disposed at the respective pixel locations in the CCD 219. During the period TC during which the electronic shutter pulse φOFD is transmitted, no signal charge is accumulated. When no electronic shutter pulse φOFD transmits or is no longer outputted, accumulation of signal charges at the respective pixel locations is started. A period TA ending with the start of an interception period (=period TE−period TC) is a substantial accumulation period.

The pulse duration or the number of electronic shutter pulses is determined based on the accumulation period during which charges are accumulated responsively to each wavelength and which is received from the CPU 23, and transmitted to the CCD 219.

For example, assume that the accumulation periods during which charges are accumulated responsively to three kinds of wavelength in the special light mode and which are stored in the memory 222 are TA(Ex1)=TE, TA(Ex2)=0.7*TE, and TA(Ex3)=0.7*TE respectively. In this case, the data representing the accumulation periods is transmitted to the CCD driving means 231 via the CPU 230. Consequently, the values of the pulse duration, during which charges are cleared, to be transmitted from the CCD driving means 231 to the CCD 219 come to OFD(Ex1)=0*TE, OFD(Ex2)=0.3*TE, and OFD(EX3)=0.3*TE respectively.

Moreover, if the accumulation periods during which charges are accumulated responsively to three kinds of wavelength in the normal light mode and which are stored in the memory 222 are TA(R)=0.7*TE, TA(G)=0.7*TE, and TA(B)= 0.7*TE respectively, the data representing the accumulation periods is transmitted to the CCD driving means 231 via the CPU 230. The values of the pulse duration, during which charges are cleared, to be transmitted from the CCD driving means 231 to the CCD 219 come to OFD(R)=OFD(G)=OFD(B)=0.3*TE.

The analog processing circuit 33 amplifies a CCD output signal of the CCD 219, and the CDS circuit performs CDS on the CCD output signal and transmits the resultant signal to the A/D converter 34. An output of the A/D converter 34 is transmitted to the digital processing circuit 235.

The digital processing circuit 235 performs various kinds of signal processing, which include clamping, white balance adjustment, color conversion, electronic zooming, gamma correction, and image enhancement, on a video signal received from the A/D converter 34. Thereafter, the digital processing circuit 235 synchronizes three video signals representing three kinds of wavelength and transmits a resultant video signal to the D/A converter 36.

The D/A converter 36 converts the video signal received from the digital processing circuit 235 from the digital form to the analog form, and transmits the resultant video signal.

The analog video signal sent from the D/A converter 36 is transmitted to the monitor 6, whereby various kinds of images are displayed. Moreover, the video signal sent from the D/A converter is transmitted to a display device or a recorder that is peripheral equipment and not shown.

The white balance adjustment and color conversion to be performed by the digital processing circuit 235 are different between the normal light mode and special light mode (narrow-band light observation). Different processes of white balance adjustment or color conversion are switched with a mode switching signal sent from the mode switching means 250.

During color conversion in the special light mode (narrow-band light observation), pixels constituting an image produced from each of three kinds of wavelength are multiplied by predetermined matrix coefficients. Consequently, a synthetic image is constructed based on three kinds of wavelength of narrow-band. Moreover, during white balance adjustment, the set values stored in the memory 222 are received by the digital processing circuit 235 via the CPU 230. Then, a white balance is attained in different manners between the normal light mode and special light mode (narrow-band light observation).

Based on a video signal received from the analog processing circuit 33, the photometry means 237 calculates an average of brightness values exhibited by a screen image represented by each of three kinds of wavelength employed in the normal light mode or special light mode (narrow-band light observation).

Moreover, in response to the mode switching signal received from the mode switching means 250, the photometry means 237 switches the methods of calculating an average of brightness values exhibited by a screen image between the normal light mode and special light mode (narrow-band light observation). In the normal light mode, the level of a luminance signal is calculated based on the average of brightness values exhibited by a screen image represented by each of three kinds of wavelength of red, green, and blue. The luminance signal is then transmitted to the diaphragm control means 42 included in the light source unit 205.

Moreover, in the special light mode (narrow-band light observation), an average of brightness values exhibited by a screen image represented by each of three kinds of wavelength Ex1, Ex2, and Ex3 is calculated. Moreover, an average of brightness values exhibited by a synthetic image produced from the three kinds of wavelength of narrow-band is calculated. The averages are transmitted to the diaphragm control means 42.

The mode switching means 250 is a switch by which an operator can freely select an observation mode either from the normal light mode or special light mode (narrow-band light observation). The mode switching means 250 may be disposed on the processor 203 or the endoscope 202, or on both of them.

The mode switching signal sent from the mode switching means 250 is transmitted to each of the rotary filter switching means 246, RGB rotary filter control means 247, photometry means 237, and digital processing circuit 235.

The RGB rotary filter 243 is interposed between the lamp 40 and condenser lens 45, and coupled to the rotation shaft of the motor 244 such that it can be rotated. The RGB rotary filter control means 247 controls or rotates the RGB rotary filter 243 at a predetermined rotating speed.

The RGB rotary filter control means 247 can freely control the rotating speed of the RGB rotary filter 243 (motor 244) according to the mode switching signal.

The RGB rotary filter control means 247 can make the rotating speed of the motor 244 in the special light mode lower than the one in the normal light mode so as to extend the exposure period.

The diaphragm control means 42 receives from the photometry means 237 the average of brightness values exhibited by a screen image, and compares the average with an operator-designated brightness value to be exhibited by an image displayed on the monitor. The diaphragm control means 42 then controls the diaphragm 41.

Incidentally, an operator can designate any brightness (target) value, which is to be exhibited by a screen image displayed on the monitor, using the brightness designating means 39 included in the light source unit 205.

Based on the result of the comparison (whether the average is larger or smaller than the operator-designated value), the diaphragm control means 42 controls the opening or closing of the diaphragm 41 interposed between the lamp 40 and RGB rotary filter 243. Consequently, an amount of light to be introduced to the back end of the light guide 12 is controlled.

The rotary filter switching means 46 selectively moves a first filter set 248 that is at the inner circumference side of the RGB rotary filter 243 and a second filter set 249 that is at the outer circumference side thereof. The rotary filter switching means 46 in the manner disposes the selected filter set on the optical axis of illumination light that links the lamp 40 and the back end of the light guide 12.

In the normal light mode, the rotary filter switching means 46 disposes the filter set 248 that is at the inner circumference side of the RGB rotary filter on the path of illumination light emanating from the lamp 40 (light P11 emanating from the lamp 40 (solid line in FIG. 16) will be incident on the filter set 248 that is at the inner circumference side of the RGB rotary filter).

In the special light mode, the rotary filter switching means 46 disposes the filter set 249 that is at the outer circumference side of the RGB rotary filter on the path of illumination light emanating from the lamp 40 (light P12 emanating from the lamp 40 (broken line in FIG. 16) will be incident on the filter set 249 that is at the outer circumference side of the RGB rotary filter).

Figure 16:
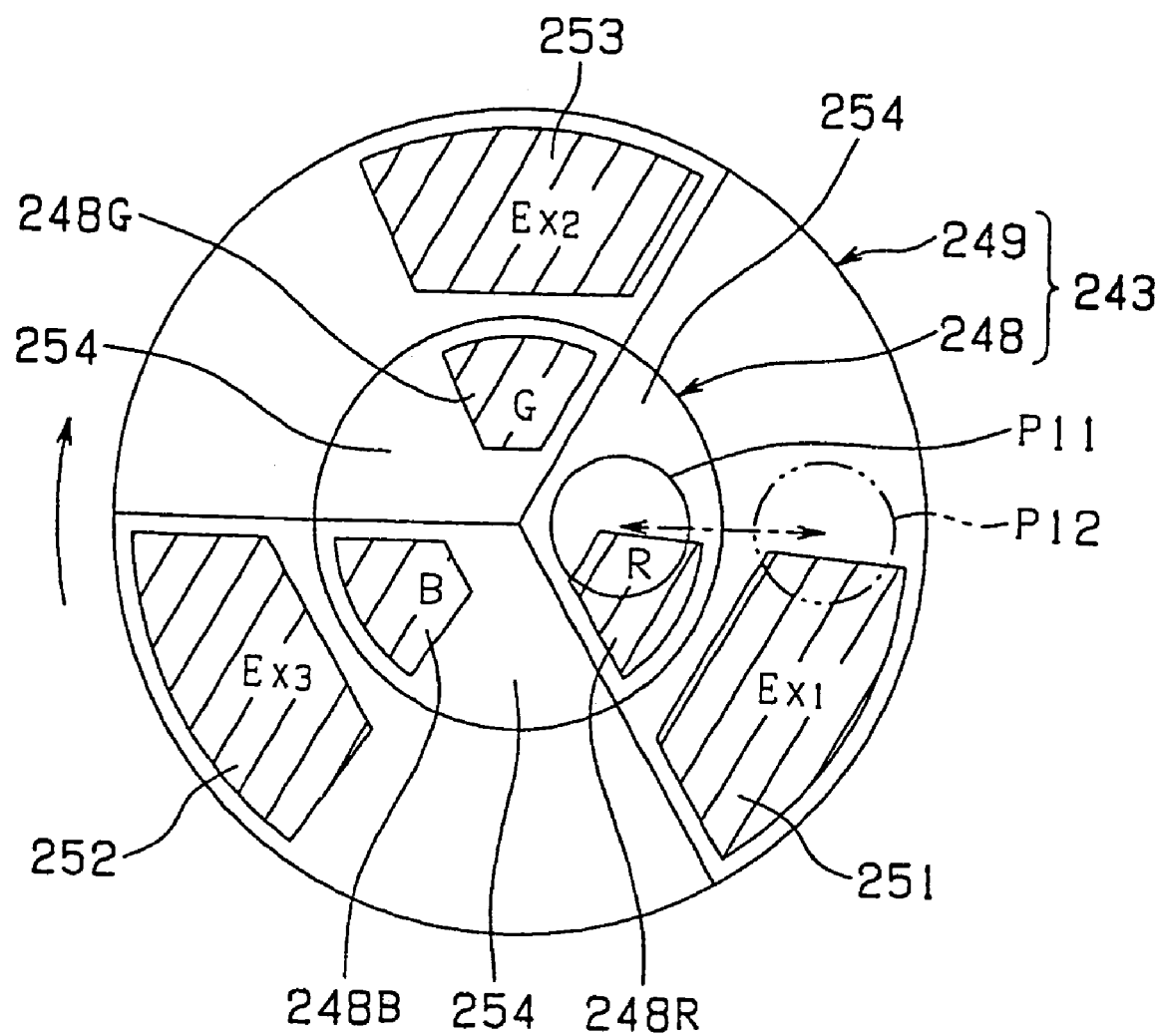

The RGB rotary filter 243 has, as shown in FIG. 16, a double structure composed of the two filter sets 248 and 249 that are the inner and outer circumference sides thereof.

The first filter set 248 that is at the inner circumference side of the RGB rotary filter comprises filters 248R, 248G, and 248B that are three filters of red, green, and blue dedicated to the normal light mode and that exhibit the spectral characteristic of passing red (R), green (G), or blue (B) band light.

The second filter set 249 that is at the outer circumference side of the RGB rotary filter comprises three filters 251, 252, and 253 that exhibit the spectral characteristic of passing a wavelength Ex1, Ex2, or Ex3 and that are dedicated to the special light mode (narrow-band light observation). The wavelengths of at least one of the three kinds of wavelength are limited to a narrow band of wavelengths. In particular, the wavelength of a blue light is limited to a narrow band.

For example, according to the present embodiment, the filter 251 for the wavelength Ex1 is a narrow-band filter that passes light whose wavelengths are centered on about 415 nm and distributed with a half width ranging from about 20 nm to about 30 nm.

The filter 252 for the wavelength Ex2 is a narrow-band filter that passes light whose wavelengths are centered on about 540 nm and distributed with a half width ranging from about 20 nm to about 30 nm.

The filter 253 for the wavelength Ex3 is a narrow-band filter that passes light whose wavelengths are centered on about 620 nm and distributed with a half width ranging from about 20 nm to about 30 nm.

Figure 17:
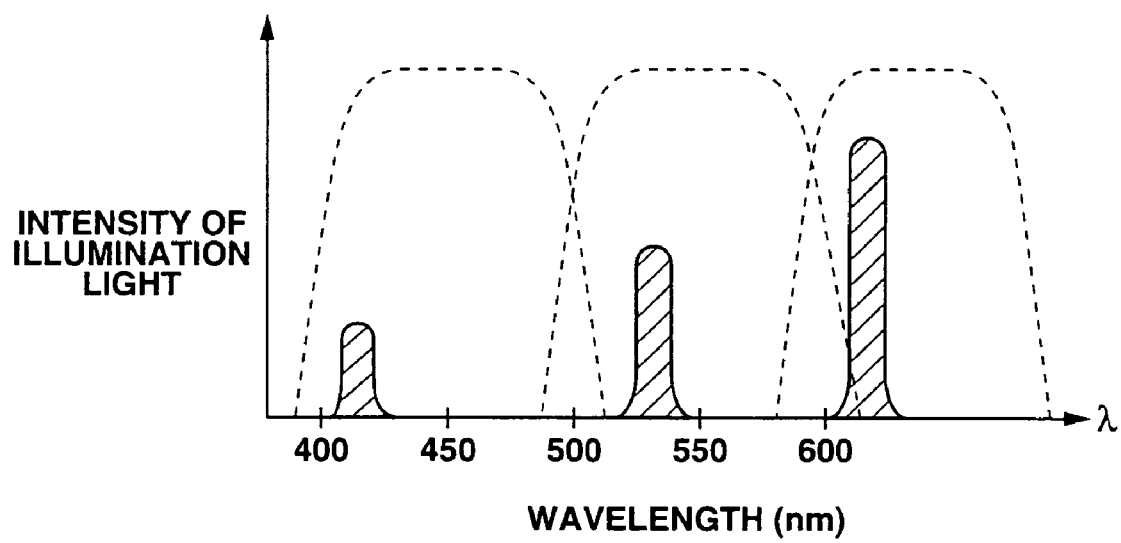

Illumination light radiated through the illumination lens 16 incorporated in the endoscope 202 via the second filter set 249 exhibits a spectral characteristic indicated with solid lines in FIG. 17.

Dashed lines in FIG. 17 indicate the spectral characteristics of three kinds of wavelength of red, green, and blue light respectively employed in normal light observation using the first filter set 248.

The size of the filters 248R, 248G, and 248B is equivalent to the exposure period during which the CCD 219 is exposed to light. The size of an interceptive portion 254 formed between adjoining ones of the filters 248R, 248G, and 248B is equivalent to an interception period (reading period) during which the CCD 219 is intercepted from light. The same applies to the second filter set 249.

Referring to FIG. 16, the normal light filters constitute the inner circumference side of the RGB rotary filter, and the special light filters constitute the outer circumference side thereof. Alternatively, the normal light filters may constitute the outer circumference side of the RGB rotary filter and the special light filters may constitute the inner circumference side thereof. Moreover, in FIG. 16, the central angle of the normal light mode filters is nearly the same as the one of the special light mode filters (narrow-band light observation). Alternatively, for example, the central angle of the special light filters may be larger than the one of the normal light filters in order to make the exposure period longer in the special light mode.

(Operation)

The usage of the endoscope apparatus 201 in accordance with the fourth embodiment will be described below.

At the start of endoscopic examination, an operator selects the endoscope 202 from among the plurality of types of endoscopes corresponding to a region to be observed, and connects the endoscope 202 to the processor 203.

The CPU 230 included in the processor 203 reads various kinds of data relevant to the endoscope 202 from the memory 222 serving as memory means via the CPU 221 included in the storage device 220 incorporated in the endoscope 202.

The data, that represents the accumulation periods, during which charges are accumulated responsively to three kinds of wavelength in the normal light mode or special light mode (narrow-band light observation) depending on the type of endoscope, and that is one of the various kinds of data, is also read from the memory 222 into the CPU 230. The data representing the accumulation periods is then transmitted to the CCD driving means 231 according to an observation mode.

Next, the operation of the endoscope apparatus in the normal light mode or special light mode (narrow-band light observation) will be described below.

An operator inserts the insertional unit 211 of the endoscope 202 into a patient's body cavity (the bronchus, esophagus, stomach, large intestine, cranio-cervix, abdominal cavity, thoracic cavity, bladder, womb, etc.) corresponding to a region to be observed, and observes the region.

For normal light observation (normal light mode), the first filter set 248 of the rotary filter 243 is disposed on the path of illumination light.

Illumination light emitted from the lamp 40 passes through the first filter set 248, whereby field-sequential illumination lights of red, green, and blue are time-sequentially irradiated to a living-body tissue through the illumination lens 16 via the light guide 12 included in the endoscope 202.

Based on the data that represents the accumulation periods during which charges are accumulated responsively to respective lights of red, green, and blue in the normal light mode and that is received from the CPU 230, the CCD driving means 231 transmits the electronic shutter pulse $\phi$OFD to the CCD 219 during the exposure period during which the CCD 219 is exposed to each of reflected lights of red, green, and blue. The CCD driving means 231 controls the pulse duration period, during which charges are cleared, so as to establish desired accumulation periods.

The endoscope 202 is a special endoscope permitting both normal light observation and special light observation. Therefore, the accumulation periods during which charges are accumulated in the CCD are shorter than those determined for a typical endoscope dedicated to normal light observation. The main reason lies in that the intensity of reflected light of narrow-band light is smaller than that of reflected light of normal light. In order to increase an amount of light incident on the light receiving surface of the CCD 219, for example, the number of optical fibers constituting the light guide 12 may be made larger than the one employed in the typical endoscope. Moreover, a clear lens may be adopted as the objective lens 17.

Therefore, during normal light observation, the intensity of light incident on the light receiving surface of the CCD 219 is larger than that in the typical endoscope. Thus, the accumulation periods during which charges are accumulated in the CCD are set according to the type of endoscope such that the magnitudes of signal charges are adjusted by making the accumulation period shorter.

The photometry means 237 calculates the level of a luminance signal, which determines the brightness of a screen image to be displayed on the monitor, and transmits the luminance signal to the diaphragm control means 42. The diaphragm control means 42 compares the luminance signal level with an operator-designated reference (target) value of brightness of an image to be displayed on the monitor. Based on the result of the comparison (whether the luminance signal level is larger or smaller), the diaphragm control means controls the opening or closing of the diaphragm 41.

If the average of brightness values exhibited by a screen image to be displayed on the monitor is larger than the reference value, the diaphragm control means causes the diaphragm 41 to move to close. On the other hand, if the average of brightness values exhibited by a screen image to be displayed on the monitor is smaller than the reference value, the diaphragm control means causes the diaphragm 41 to move to open. Consequently, the intensity of light to be irradiated to a living-body tissue is varied such that the average of brightness values exhibited by an image to be displayed on the monitor 6 will be retained at the operator-designated value. Automatic light adjustment operation is thus achieved by controlling the diaphragm 41.

Lights of red, green, and blue reflected from a living-body tissue sequentially are incident on the CCD 219. CCD output signals produced responsively to the reflected lights of red, green, and blue are inputted to the signal processing unit 204. The analog processing circuit 33 and digital processing circuit 235 perform various kinds of signal processing. Eventually, a normal light image is displayed on the monitor 6 or recorded in peripheral equipment such as a personal computer.

For narrow-band light observation (special light mode), an operator having been engaged in normal light observation selects the special light mode (narrow-band light observation) by manipulating a mode selection switch that constitutes the mode switching means 250 provided on the endoscope 202 or processor 203. The rotary filter switching means 246 is activated synchronously with the manipulation, and the second filter set 249 of the RGB rotary filter 243 is disposed on the path of illumination light.

Illumination light emitted from the lamp 40 included in the light source unit 205 passes through the second filter set 249 of the RGB rotary filter 243. Consequently, blue-band light passing through the filter Ex1, green narrow-band light passing through the filter Ex2, and red narrow-band light passing through the filter Ex3 are incident on to the back end of the light guide 12 through the condenser lens 45. Eventually, illumination light exhibiting the spectral characteristic (spectrum and intensity) indicated in FIG. 17 is time-sequentially irradiated to a living-body tissue through the illumination lens 16 incorporated in the distal section 215 of the endoscope 202.

Based on the data that represents the accumulation periods during which charges are accumulated responsively to red narrow-band light, green narrow-band light, and red narrow-band light respectively in the special light mode (narrow-band light observation) and that is received from the CPU 230, the CCD driving means 231 controls the pulse duration during which charges are cleared. The CCD driving means 231 thus controls the accumulation periods during which charges are accumulated in the CCD 219 responsively to each image picking-up of the three kinds of wavelength.

The accumulation period during which charges are accumulated responsively to blue narrow-band light out of three lights is longer than the accumulation periods during which charges are accumulated responsively to green and red narrow-band lights respectively. Therefore, the pulse duration is set to a larger value for green or red narrow-band light than for blue narrow-band light.

Figure 18:
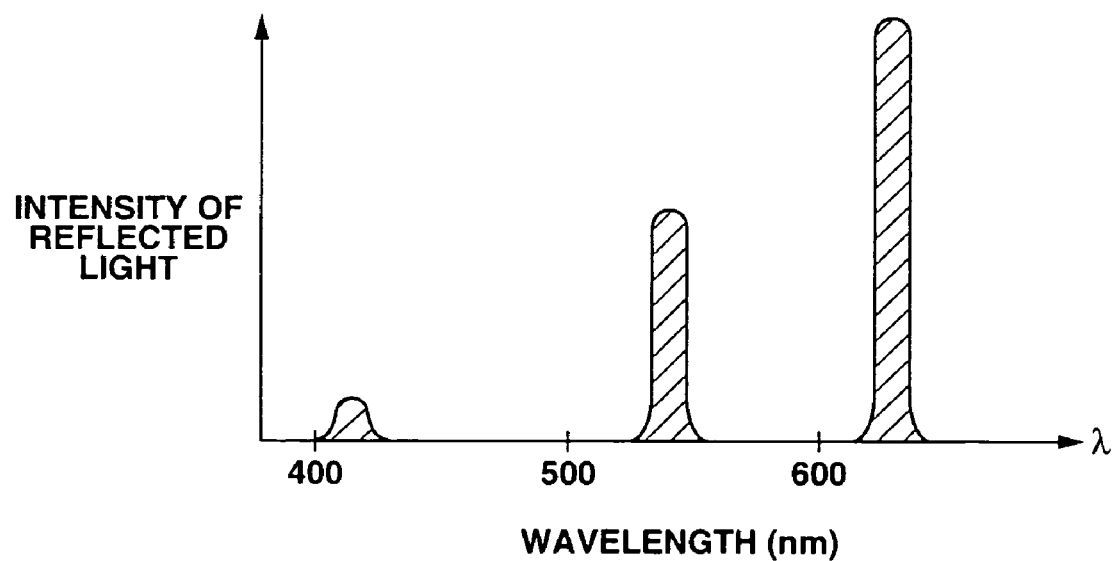

The intensity of blue narrow-band reflected light is much smaller than those of narrow-band reflected lights of green and red. For example, assuming that illumination light indicated in FIG. 17 is irradiated to a living-body tissue, reflected light as indicated in FIG. 18 will be obtained. The band of wavelengths centered on 415 nm is an absorption band relative to hemoglobin, and light reflected from a living-body tissue exhibits a unique spectral characteristic. Moreover, the ratio of the intensities of the three kinds of wavelength varies depending on a region. Now, a description will be made on the assumption that the ratio of the intensity of blue narrow-band light to that of green narrow-band light to that of red narrow-band light is 1:5:10.

As the accumulation periods TA during which charges are accumulated responsively to each wavelength in the special light mode, for example, the accumulation period TE during which charges are accumulated responsively to blue narrow-band light, the accumulation period 0.2*TE during which charges are accumulated responsively to green reflected light, and the accumulation period 0.1*TE during which charges are accumulated responsively to red reflected light are stored in the memory 222. When the images formed by the three kinds of wavelength are picked up during the respective accumulation periods, an average of brightness values exhibited by a screen image represented by a wavelength is nearly the same among the three kinds of wavelength. The image formed by blue narrow-band light is picked up during the longer accumulation period than the green and red narrow-band lights are.

The photometry means 237 calculates an average of brightness values exhibited by a screen image to be displayed on the monitor, that is, a synthetic image produced from the three kinds of wavelength. The calculated value is transmitted to the diaphragm control means 42. The diaphragm control means 42 compares the average of brightness values exhibited by a synthetic image with an operator-designated reference (target) value of brightness. Based on the result of the comparison (whether the average is larger or smaller), the diaphragm control means 42 controls the opening or closing of the diaphragm 41.

For example, if the average of brightness values exhibited by a screen image to be displayed on the monitor is larger than the reference value, the diaphragm control means 42 causes the diaphragm 41 to move to close. On the other hand, if the average of brightness values exhibited by a screen image to be displayed on the monitor is smaller than the reference value, the diaphragm control means 42 causes the diaphragm 41 to move to open. Consequently, by varying the intensity of light to be irradiated to a living-body tissue, the brightness of an image displayed on the monitor 6 can be retained at the operator-designated value. Thus, automatic light adjustment operation is achieved by controlling the diaphragm 41.

Lights reflected from a living-body tissue to which blue narrow-band light, green narrow-band light, and red narrow-band light indicated in FIG. 18 are incident are then incident on the light receiving surface of the CCD 219 via the objective lens 17. The lights sequentially enter the CCD 219. CCD output signals produced responsively to the three kinds of wavelength are inputted to the signal processing unit 204. The analog processing circuit 33 and digital processing circuit 235 perform various kinds of signal processing on the CCD output signals. Consequently, a fluorescence image is displayed on the monitor 6 or recorded in peripheral equipment such as a personal computer.

Moreover, the digital processing circuit 235 switches the white balance coefficients associated with three kinds of wavelength to the set values that are stored in the memory 222 and that are determined for the special light mode (narrow-band light observation) which is different from the normal light mode.

Moreover, for color conversion, the pixels of an image produced from each three kinds of wavelength are multiplied by predetermined matrix coefficients in order to construct a synthetic image on the basis of the three kinds of wavelength.

Compared with normal light observation, narrow-band light observation is characterized by sharp visualization of the fine structure and the capillary vessels of the mucosal surface (shallow layer) of, for example, the alimentary track. This is achieved by irradiating narrow-band light whose wavelengths fall within the blue region (short wavelengths) to a living-body tissue.

Namely, the degree of propagation of light in a mucosal depth direction is wavelength-dependent. The shorter the wavelength of light, the smaller the degree of propagation of the light in the depth direction (the shallower the region to which the light is propagated). Moreover, the band of wavelengths centered on 415 nm is a large absorption band relative to hemoglobin in the mucosa (living body). Therefore, when light whose wavelengths fall within a narrow band ranging from 400 to 450 nm is irradiated to the mucosa, the fine structure and the capillary vessels of the mucosal surface can be uniquely visualized.

Consequently, the structure of the mucosal surface and the running pattern of the capillary vessels that are very hard to observe under normal light can be quite clearly visualized through narrow-band light observation.

An operator observes in detail the fine structure of the mucosal surface or the running pattern of the capillary vessels through, for example, enlargement observation. Consequently, the operator can easily and qualitatively diagnose whether a lesion is neoplastic or non-neoplastic or a tumor is benign or malignant.

(Advantages)

The present embodiment provides advantages described below.

According to the present embodiment, in the special light mode (narrow-band light observation), when images formed by reflected lights of narrow-band light of blue, green, and red whose intensities are largely different from one another are picked up, the accumulation period during which charges are accumulated in the CCD responsively to a wavelength is determined differently among the three kinds of wavelength. Consequently, images represented by each wavelength are formed with appropriate brightness.

According to the present embodiment, a synthetic image whose brightness is more appropriate and whose quality is higher can be constructed.

Fifth Embodiment

Figure 19:
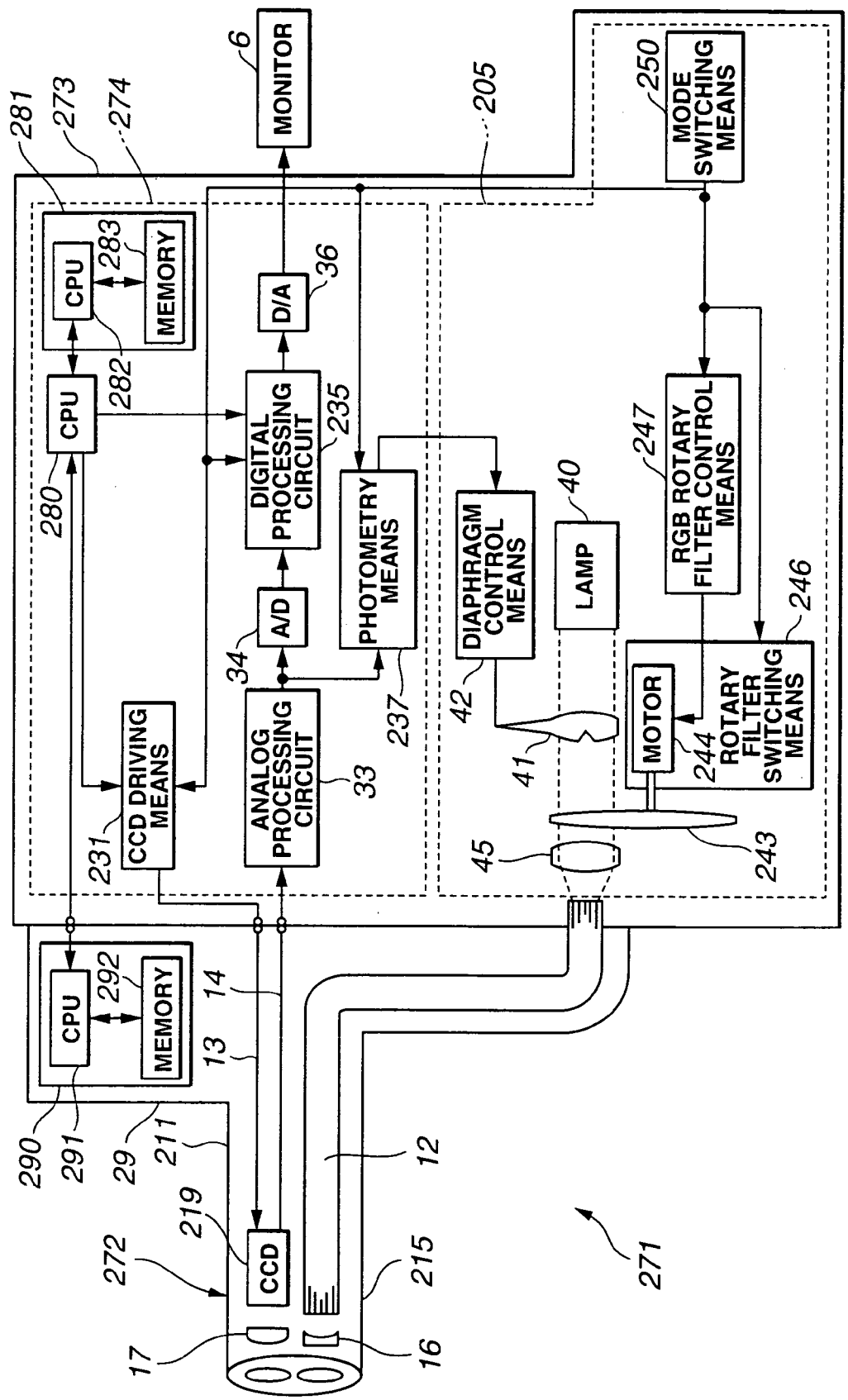
FIG. 19 is a block diagram schematically showing the configuration of an endoscope apparatus in accordance with a fifth embodiment of the present invention.

FIG. 19 is a block diagram schematically showing the configuration of an endoscope apparatus in accordance with a fifth embodiment of the present invention. The same reference numerals will be assigned to components identical to those of the fourth embodiment shown in FIG. 14 to FIG. 18, and the description of the components will be omitted.

(Configuration)

In the fourth embodiment shown in FIG. 14 to FIG. 18, the memory means in which the data representing the accumulation periods during which charges are accumulated responsively to three kinds of wavelength and which are different among the plurality of types of endoscopes is stored is incorporated in the endoscope. In an endoscope apparatus 271 of the fifth embodiment, the memory means in which the data representing the accumulation periods is stored is incorporated in a processor 273.

A storage device 281 is included in a signal processing unit 274 incorporated in the processor 273.

The storage device 281 comprises a CPU 282 and a memory (EEPROM) 283 that is memory means.

The memory 283 is a nonvolatile memory in which data is stored.

The CPU 282 controls reading or writing of data from or to the memory 283, and also controls transmission or reception (communication) of data to or from a CPU 280 incorporated in the processor 273.

The accumulation periods (electronic shutter speeds) during which charges are accumulated responsively to three kinds of wavelength of red, green, and blue in the normal light mode are stored in the memory 283. Moreover, the accumulation periods (electronic shutter speeds) during which charges are accumulated responsively to three kinds of wavelength Ex1, Ex2, and Ex3 in the special light mode (narrow-band light observation) are stored in the memory 283.

Instead of the accumulation periods, a charge clear period or the ratio of the accumulation periods during which charges are accumulated responsively to three kinds of wavelength may be stored in the memory 283.

The accumulation periods during which charges are accumulated responsively to three kinds of wavelength of red, green, and blue in the normal light mode and which are stored in the memory 283 are shorter than those determined relative to a typical endoscope dedicated to normal light observation.

As the accumulation periods during which charges are accumulated responsively to three kinds of wavelength in the special light mode (narrow-band light observation) and which are stored in the memory 283, the accumulation periods optimal to a plurality of types of endoscopes (for examination of the bronchus, superior alimentary tract, inferior alimentary tract, cranio-cervix, and bladder) are set. This is because the intensities of the three narrow-band lights of three kinds of wavelength obtained from every region vary depending on the region. The accumulation periods during which charges are accumulated responsively to three kinds of wavelength are therefore set region by region such that the intensities of the lights will be nearly equal among the regions.

A storage device 290 is incorporated in an endoscope 272. The storage device 290 comprises a CPU 291 and a memory (EEPROM or the like) 292.

The memory 292 is a nonvolatile memory in which data is stored.

The CPU 291 controls reading or writing of data from or to the memory 292, and also controls transmission or reception (communication) of data to or from the CPU 280 incorporated in the processor 273.

Moreover, various kinds of data relevant to the endoscope are stored in the memory 292.

Namely, the various kinds of data stored in the memory 292 include an endoscope model (type) name, an endoscope serial number, white balance set values (for normal light and for special light (narrow-band light observation)), the number of periods by which the endoscope is connected to the processor and the power supply of the endoscope is turned on, information on a forceps channel included in the endoscope, the outer diameter of the distal section of the endoscope, and the outer diameter of the insertional unit of the endoscope.

The CPU 280 is incorporated in the signal processing unit 274. The CPU 280 extends control to read the various kinds of data relevant to the endoscope, which are stored in the memory 292, via the CPU 291. The CPU 280 also extends control via the CPU 282 so as to read the data that represents the accumulation periods, during which charges are accumulated responsively to three respective light waves in the normal light mode or special light mode (narrow-band light observation), and that is stored in the memory 283.

The CPU 280 judges the type of endoscope 272 (for examination of the bronchus, superior alimentary tract, inferior alimentary tract, or cranio-cervix) connected to the processor 273 from various kinds of data read from the memory 292. The CPU 280 reads the data, which represents the accumulation periods during which charges are accumulated responsively to three kinds of wavelength in the normal light mode or special light mode and which are related to the type of connected endoscope 272, from the memory 283. The CPU 280 then transmits the data to the CCD driving means 231.

Moreover, the other items of the endoscope model name, serial number, and white balance set values (for normal light and for special light) are transmitted to the digital processing circuit 235.

Consequently, when the endoscope 272 is connected to the processor 273, various kinds of data stored in the memory 292 are read into the CPU 280 via the CPU 291. Moreover, the data representing the accumulation periods and being stored in the memory 283 is read into the CPU 280 via the CPU 282.

(Operation)

The usage of the endoscope apparatus 271 in accordance with the fifth embodiment will be described below.

At the start of endoscopic examination, an operator selects the endoscope 272 from among the plurality of types of endoscopes corresponding to a region to be observed, and connects the endoscope to the processor 273. The CPU 280 incorporated in the processor 273 reads various kinds of data relevant to the endoscope 272 from the memory 292 via the CPU 291 included in the storage device 290 incorporated in the endoscope 272.

The CPU 280 judges the type of endoscope 272 connected to the processor 273 (for examination of the bronchus, superior alimentary tract, inferior alimentary tract, or cranio-cervix) from the various kinds of data read from the memory 292. The CPU 280 reads from the memory 283 the data that represents the accumulation periods during which charges are accumulated responsively to three kinds of wavelength in the normal light mode or special light mode (narrow-band light observation) and which are related to the type of endoscope 272. The CPU 280 then outputs the data to the CCD driving means 231. The CCD driving means 231 drives or controls the CCD 219 according to a mode switching signal sent from the mode switching means 250.

(Advantages)

The present embodiment provides advantages described below.

According to the fifth embodiment, in the special light mode (narrow-band light observation), when images formed by a plurality of reflected lights whose intensities are greatly different from one another are picked up, the images formed by the reflected lights are picked up during different accumulation periods respectively. Consequently, images represented by the reflected lights are picked up with appropriately brightness. Eventually, a synthetic image can be constructed with more appropriate brightness and higher image quality. Moreover, the data representing the accumulation periods during which charges are accumulated in the normal light mode or special light mode (narrow-band light observation) is stored in the memory means incorporated in the processor. Therefore, the storage capacity of the memory means incorporated in the endoscope may be reduced accordingly.

Sixth Embodiment

Figure 20:
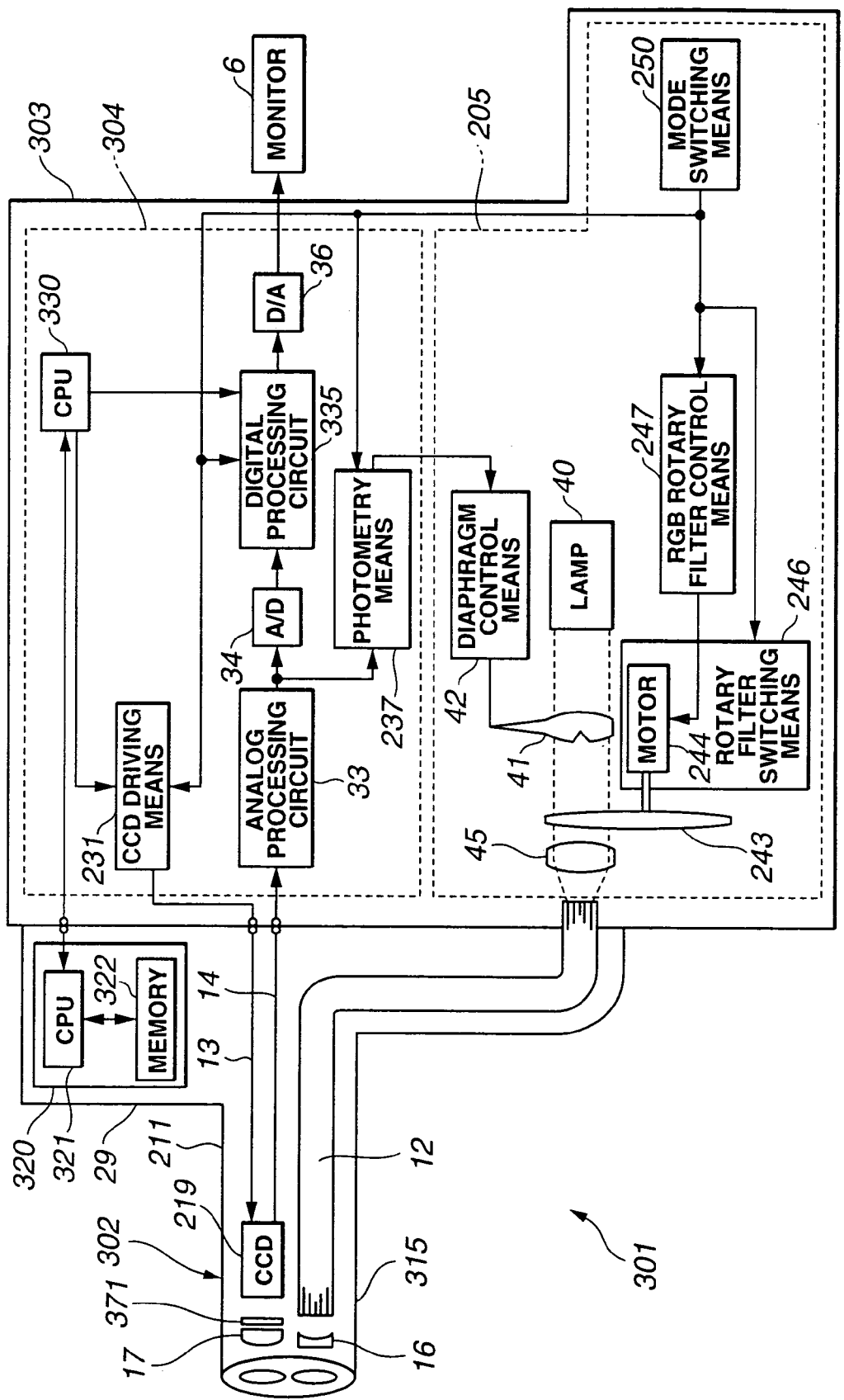
FIG. 20 is a block diagram schematically showing the configuration of an endoscope apparatus in accordance with a sixth embodiment of the present invention.

FIG. 20 is a block diagram schematically showing the configuration of an endoscope apparatus in accordance with a sixth embodiment of the present invention. The same reference numerals will be assigned to components identical to those of the fourth embodiment shown in FIG. 14 to FIG. 18.

(Configuration)

As shown in FIG. 20, an endoscope apparatus 301 in accordance with the sixth embodiment comprises, in addition to the same components as those of the fourth embodiment shown in FIG. 14 to FIG. 18, spatial frequency characteristic converting means (pupil modulation element) and spatial frequency characteristic restoring means.

In an insertional unit 311 of the endoscope apparatus 301, a spatial frequency characteristic converting means 371 is interposed between the objective lens 17 and the CCD 219.

The spatial frequency characteristic converting means 371 and spatial frequency characteristic restoring means adopt the technology described in relation to the spatial frequency characteristic converting means 171 and spatial frequency characteristic restoring means described relative to the third embodiment in conjunction with FIG. 13.

A digital processing circuit 335 is identical to the digital processing circuit 235 employed in the fourth embodiment except that the digital processing circuit 335 newly includes spatial frequency characteristic restoring means.

The spatial frequency characteristic converting means 371 utilizes the property of a rotationally asymmetric optical element of causing a rotationally asymmetric blur (rotationally asymmetric aberration).

The spatial frequency characteristic restoring means performs logical or arithmetic operations only when spatial frequency characteristic restoration data is stored in the memory 322.

A storage device 320 comprises a CPU 321 and a nonvolatile memory 322.

The memory 322 is formed with an EEPROM or the like and nonvolatile. In addition to various kinds of data employed in the fourth embodiment, spatial frequency characteristic restoration data is stored in the memory 322 in relation to each of types of endoscopes.

Stored as the spatial frequency characteristic restoration data in the memory 322 are the same values shared between the normal light mode and special light mode (narrow-band light observation).

The CPU 321 controls reading or writing of data from or to the memory 322, and also controls transmission or reception (communication) of data to or from a processor 303.

A CPU 130 reads spatial frequency characteristic restoration data (filtering coefficients) from the memory 322 via the CPU 321, and transmits the data to the digital processing circuit 335.

(Operation)

The usage of the endoscope apparatus 301 in accordance with the sixth embodiment will be described below.

At the start of endoscopic examination, an operator selects an endoscope 302 from among the plurality of types of endoscopes corresponding to a region to be observed, and connects the endoscope to the processor 303.

The CPU 330 incorporated in the processor 303 reads various kinds of data relevant to the endoscope 302 from the memory 322 via the CPU 320 included in the storage device 320 incorporated in the endoscope 302. Spatial frequency characteristic restoration data (filtering coefficients) associated with the type of connected endoscope, which is one of the various kinds of data, is read from the memory 322 into the CPU 330, and then transmitted to the digital processing circuit 335.

During normal light observation, three kinds of wavelength of red, green, and blue reflected from a living-body tissue sequentially are incident on the CCD 219 via the objective lens 17 and spatial frequency characteristic converting means 371. During narrow-band light observation, blue, green, and red lights reflected from a living-body tissue sequentially are incident on the CCD 219 via the objective lens 17 and spatial frequency characteristic converting means 371.

CCD output signals produced responsively to each light are transmitted to the signal processing unit 304. When the spatial frequency characteristic converting means 371 is incident on, compared with when the spatial frequency characteristic converting means 371 is absent, an image represented by an image signal sent to the signal processing unit 304 is blurred.

The digital processing circuit 335 included in the signal processing unit 304 uses spatial frequency characteristic restoration data, which is received via the CPU 330 and read from the memory 322, to perform spatial filtering. Namely, the digital processing circuit 335 multiplies peripheral pixels of each pixel by filtering coefficients for use in restoring a spatial frequency characteristic.

Consequently, the spatial frequency characteristic converting means 371 restores a blurred image to its original state. Other predetermined signal processing is also performed. Eventually, a normal light image is displayed on the monitor 6 or recorded in peripheral equipment such as a recording means.

(Advantages)

The present embodiment provides advantages described below.

According to the sixth embodiment, the same advantages as those of the fourth embodiment are provided. In addition, since the spatial frequency characteristic converting means is included, an f-number signifying an objective lens included in an optical system can be decreased while a conventionally ensured depth of field is maintained (a clear lens can be adopted).

Consequently, according to the sixth embodiment, even if the intensity of light reflected from an object is the same, the intensity of light incident on a CCD can be increased. In particular, even when an object image represented by reflected light whose intensity is low is acquired, image quality supported with a high signal-to-noise ratio can be attained.

According to the fourth to sixth embodiments, the accumulation periods determined for the normal light mode and special light mode (narrow-band light observation) respectively may be stored in the memory means incorporated in the processor. Spatial frequency characteristic restoration data may be stored in the memory means incorporated in the endoscope.

According to the fourth to sixth embodiments, the CCD is adopted as an image sensor. Alternatively, a rear-side incidence CCD, a CMOS image sensor, or a sensitivity-valiable CCD employed in the first to third embodiments may be adopted.

According to the fourth to sixth embodiments, a CCD that is a solid-state image-pickup device is incorporated in the distal section of the endoscope. Alternatively, two CCDs may be incorporated in the distal section of the endoscope. A first CCD may be dedicated to the normal light mode, and a second CCD may be dedicated to the special light mode. In this case, CCD switching means that is formed with a relay or the like and that produces a CCD driving signal and a reading signal may be incorporated in the endoscope or contained in a cable linking the endoscope and processor. Then the CCD corresponding to each observation mode may be driven or read according to a mode switching signal sent from the mode switching means. Incidentally, driving/reading circuits corresponding to the two CCDs may be included in the processor.

According to the fourth to sixth embodiments, three kinds of wavelength employed in the special light mode are narrow-band lights of blue, green, and red. Selections of wavelengths of limited narrow bands, the centered wavelength or various combinations thereof are possible. The combinations include, for example, a combination of three narrow-band lights whose wavelengths fall within the blue region, a combination of two narrow-band lights whose wavelengths fall within the blue region and green region respectively, a combination of narrow-band light whose wavelengths fall within the blue region and broad-band light whose wavelengths fall within the green region and are distributed with a large half width.

According to the fourth to sixth embodiments, the filters that pass three kinds of wavelength employed in the special light mode are included in the second filter set of the RGB rotary filter. An optional filter may be adopted such that when the special light mode is designated, the optional filter will be inserted to a light path linking the lamp and condenser lens.

The optional filter is a filter having a property of transmitting three narrow-band lights whose wavelengths fall within, for example, the blue, green, and red regions respectively. The optional filter is used in combination with the first filter set of the RGB rotary filter dedicated to normal light observation.

Illumination light emitted from the lamp is divided into narrow-band lights of blue, green, and red by means of the optional filter. The narrow-band lights of blue, green, and red are passed through the broad-band filters for red, green, and blue constituting the first filter set dedicated to normal light. Consequently, the narrow-band lights whose wavelengths fall within the blue, green, and red regions respectively are time-sequentially incident on the light guide and sequentially irradiated to an object through the objective lens.

Consequently, the same advantage as the one resulting from the employment of the second filter described in relation to the fourth to sixth embodiments can be provided.

Incidentally, the lights of blue, green, and red employed in the special light mode may not be limited to narrow-band lights. Various types of selections and combinations of the narrow-band wavelength, the central wavelength, the half width of the distribution of wavelengths, or the like, are applicable.

According to the fourth to sixth embodiments, special wavelength employed in the special light mode is reflected light of narrow-band lights whose wavelengths fall within the visible region. Alternatively, the reflected light may be reflected light of narrow-band lights whose wavelengths fall within the ultraviolet region or the near infrared to infrared region thereof. For example, the fourth to sixth embodiments can be adapted to infrared light observation. For the infrared light observation, since a wavelength band around 800 nm is the absorption band relative to indocyanine green (ICG), the ICG is intravenously injected into a living-body tissue. Plural kinds of wavelength whose wavelengths fall within a band centered on 800 nm (for observation of the degree of ICG absorption) and a band centered on 900 nm (filling the role of reference light) respectively are then irradiated to the living-body tissue. The reflected lights are observed. In this case, various combinations are conceivable as the combination of wavelength to be irradiated that are different from one another in terms of the wavelength or the wavelength band.

According to the fourth to sixth embodiments, the CCD is incorporated in the distal section of the endoscope. Alternatively, the CCD may be disposed outside a fiberscope having an image fiber bundle by which an optical image is transmitted into the endoscope (any place other than the insertional unit of the endoscope). A hybrid endoscope may be constructed with the CCD integrated into it, or the CCD may not be integrated into the endoscope but may be freely detachable or attachable from or to the endoscope.

In order to pick up images formed by narrow-band light, of which intensity is lower than that of normal light, at a higher signal-to-noise ratio, the accumulation period during which charges are accumulated responsively to the incident narrow-band light may be extended. Otherwise, a pixel binning reading technique or the like for adding up peripheral pixels of each pixel in a CCD may be adopted in combination.

As described so far, according to the present invention, observation can be performed based on information optimal to a type of endoscope. In the special light mode, when images formed by a fluorescence and a plurality of reflected lights whose intensities are greatly different from one another are picked up, the accumulation period during which charges are accumulated in the CCD is varied depending on the lights. Consequently, images represented by the respective lights can be formed with a nearly equal level of brightness.

Consequently, according to the present invention, images represented by respective lights can be formed with appropriate brightness, and a special light image that is a synthetic image constructed based on the images can enjoy high image quality.

Moreover, according to the present invention, an output signal of an image pickup device is restored to its original state according to restoration data stored in memory means. While a conventionally attained depth of field is maintained, an f-number signifying an objective lens included in an optical system can be reduced. Namely, even when the intensity of light reflected from an object is the same, the intensity of light incident on a CCD can be increased. In particular, even when feeble light forms images on the CCD, high image quality supported with a high signal-to-noise ratio can be ensured.

Having described the preferred embodiments of the invention referring to the accompanying drawings, it should be understood that the present invention is not limited to those precise embodiments and various changes and modifications thereof could be made by one skilled in the art without departing from the spirit or scope of the invention as defined in the appended claims.

What is claimed is:

1. An endoscope apparatus having a solid-state image-pickup device that picks up images of an object, comprising:
    an endoscope including the solid-state image-pickup device in which charges are accumulated in order to pick up an image of the object during an accumulation period;
    a memory in which a plurality of pieces of information on the accumulation period, during which charges are accumulated in the solid-state image-pickup device, is stored;
    a drive unit that controls the accumulation period, during which charges are accumulated in the solid-state image-pickup device, according to the pieces of information on the accumulation period stored in the memory;
    an optical member which is included in an optical system that forms an optical image on the solid-state image-pickup device and whose surface is shaped rotationally asymmetric;
    a correction information memory in which correction information associated with the optical property of the optical member is stored; and
    a correction unit that corrects an output signal of the solid-state image-pickup device according to the contents of the correction information memory.

2. The endoscope apparatus according to claim 1, wherein the pieces of information on the accumulation period are determined for respective wavelength bands of images formed by lights to be picked up by the solid-state image-pickup device.

3. An endoscope apparatus according to claim 1, wherein: a first image pickup mode in which normal light whose wavelengths fall within the visible region is employed, a second image pickup mode in which special light whose wavelengths fall within a band different from the wavelength band of normal light is employed, and the pieces of information on the accumulation period are determined relative to each of the first image pickup mode and second image pickup mode.

4. The endoscope apparatus according to claim 1, wherein the solid-state image-pickup device includes a facility for multiplying produced charges with application of a pulse-type signal so as to vary the sensitivity of the solid-state image-pickup device.

5. The endoscope apparatus according to claim 4, wherein the solid-state image-pickup device includes a charge multiplying detector that multiplies produced charges through impact ionization derived from application of the pulse-type signal by controlling the amplitude of the pulse-type signal or the number of pulses of the pulse-type signal, and that thus varies the sensitivity of the solid-state image-pickup device.

6. The endoscope apparatus according to claim 5, wherein the charge multiplying detector is interposed between a horizontal transfer register and a floating diffusion amplifier that are incorporated in the solid-state image-pickup device, or disposed at each of pixel locations in the solid-state image-pickup device.

7. The endoscope apparatus according to claim 1, further comprising a light source unit that illuminates the object.

8. The endoscope apparatus according to claim 7, wherein the light source unit illuminates the object by switching normal light employed in normal light observation and a plurality of special lights employed in special light observation.

9. The endoscope apparatus according to claim 8, wherein the special light observation refers to fluorescence observation employing fluorescence.

10. The endoscope apparatus according to claim 8, wherein the plurality of special lights include blue excitation light to be used for fluorescence and narrow-band lights whose wavelengths fall within the green or red region to be used for reflected light.

11. The endoscope apparatus according to claim 8, wherein the special light observation refers to narrow-band light observation employing narrow-band light.

12. The endoscope apparatus according to claim 8, wherein the plurality of special lights include lights whose wavelengths fall within the blue, green, or red region, and at least one of the lights whose wavelengths fall within the blue, green, or red region is narrow-band light.

13. The endoscope apparatus according to claim 8, wherein the special light observation refers to infrared light observation employing infrared light.

14. The endoscope apparatus according to claim 8, wherein the plurality of special lights include light whose wavelengths fall within the near infrared region.

15. The endoscope apparatus according to claim 1, wherein a plurality of illumination periods occur, the plurality of acclumation periods refers to accumulation periods during which charges are accumulated responsively to a plurality of lights respectively during special light observation.

16. The endoscope apparatus according to claim 15, wherein the special light observation refers to fluorescence observation employing fluorescence.

17. The endoscope apparatus according to claim 16, wherein during the fluorescence observation, the accumulation period during which charges are accumulated responsively to fluorescence is different from the accumulation period during which charges are accumulated responsively to reflected light.

18. The endoscope apparatus according to claim 17, wherein the accumulation period during which charges are accumulated responsively to fluorescence is longer than the accumulation period during which charges are accumulated responsively to reflected light.

19. The endoscope apparatus according to claim 15, wherein the special light observation refers to narrow-band light observation employing narrow-band light.

20. The endoscope apparatus according to claim 19, wherein the accumulation period during which charges are accumulated responsively to narrow-band light, of which wavelengths fall within the blue region, during narrow-band light observation is longer than the accumulation period during which charges are accumulated responsively to narrow-band light of green or red.

21. The endoscope apparatus according to claim 8, wherein the special light observation refers to infrared light observation employing infrared light.

22. The endoscope apparatus according to claim 1, wherein a plurality of illumination periods occur, the plurality of accumulation periods refers to accumulation periods during which charges are accumulated responsively to respective lights of red, green, and blue in a normal light mode.

23. The endoscope apparatus according to claim 1, wherein a plurality of illumination periods occur, the plurality of accumulation periods refers to accumulation periods during which charges are accumulated responsively to respective lights of red, green, and blue in a normal light mode or responsively to plural kinds of wavelength during a special light mode.

24. The endoscope apparatus according to claim 1, further comprising a sensitivity control unit that controls an amplification factor, at which charges in the solid-state image-pickup device are amplified, by varying a pulse-type signal.

25. The endoscope apparatus according to claim 24, wherein the sensitivity control unit includes an automatic gain control circuit that increases or decreases the amplification factor, at which charges in the solid-state image-pickup device are amplified, by controlling the amplitude of an applied pulse such that an output signal of the solid-state image-pickup device will assume a predetermined level during special light observation.

26. The endoscope apparatus according to claim 1, wherein the drive unit applies to the solid-state image-pickup device arm electronic shutter signal that releases charges accumulated in the solid-state image-pickup device during an exposure period longer than a designated accumulation period, and thus the drive unit controls and sets the accumulation period as an alternative designated accumulation period that is longer that the designated accumulation period.

27. The endoscope apparatus according to claim 1, wherein the memory is incorporated in the endoscope.

28. An endoscope for picking up an object image, comprising:
   a solid-state image-pickup device in which charges are accumulated in order to pick up an image of the object;
   a memory in which a plurality of pieces of information on the accumulation period during which charges are accumulated in the solid-state image-pickup device are stored in order to transmit the pieces of information on the accumulation period to driving means that controls the accumulation period during which charges are accumulated in the solid-state image-pickup device;
   an optical member which is included in an optical system that forms an optical image on the solid-state image-pickup device and whose surface is shaped rotationally asymmetric;
   a correction information memory in which correction information associated with the optical property of the optical member is stored; and
   a correction unit that corrects an output signal of the solid-state image-pickup device according to the contents of the correction information memory.

29. An endoscope apparatus including a solid-state image-pickup device for picking up an object image, comprising:
   an endoscope having the solid-state image-pickup device in which charges are accumulated in order to pick up an image of an object;
   memory means in which a plurality of pieces of information on the accumulation period during which charges are accumulated in the solid-state image-pickup device is stored;
   driving means for controlling the accumulation period, during which charges are accumulated in the solid-state image-pickup device, on the basis of the pieces of information on the accumulation period stored in the memory means;
   an optical member which is included in an optical system that forms an optical image on the solid-state image-pickup device and whose surface is shaped rotationally asymmetric;
   a correction information memory in which correction information associated with the optical property of the optical member is stored; and
   a correction unit that corrects an output signal of the solid-state image-pickup device according to the contents of the correction information memory.

30. An endoscope apparatus including an image pickup device for picking up an object image, comprising:
   an endoscope having the image pickup device that picks up an image of the object and an optical system that includes an optical member whose surface is shaped rotationally asymmetric;
   a memory in which restoration data for use in restoring a change in optical performance caused by the optical member is stored; and
   a signal processing unit that restores an output signal of the image pickup device to its original state on the basis of the restoration data stored in the memory and that performs signal processing.

31. An endoscope apparatus including an image pickup device for picking up an object, comprising:
   an endoscope having an image pickup device that picks up an image of the object and an optical system that includes an optical member whose surface is shaped rotationally asymmetric;
   a memory in which a plurality of pieces of information on the accumulation period during which charges are accumulated in the image pickup device and restoration information for use in restoring a change in optical performance caused by the optical member are stored;
   a drive unit that controls the accumulation period, during which charges are accumulated in the image pickup device, on the basis of the pieces of information on the accumulation period stored in the memory; and
   a signal processing unit that performs signal processing to restore an output signal of the image pickup device to its original state on the basis of the restoration information stored in the memory.

* * * * *